(12) United States Patent
Hayashi

(10) Patent No.: US 9,665,254 B2
(45) Date of Patent: May 30, 2017

(54) RADIOGRAPHIC IMAGE CAPTURING SYSTEM AND CONSOLE

(71) Applicant: Konica Minolta, Inc., Tokyo (JP)

(72) Inventor: Naoki Hayashi, Higashimurayama (JP)

(73) Assignee: KONICA MINOLTA INC., Tokyo (JP)

( * ) Notice: Subject to any disclaimer, the term of this patent is extended or adjusted under 35 U.S.C. 154(b) by 127 days.

(21) Appl. No.: 14/520,924

(22) Filed: Oct. 22, 2014

(65) Prior Publication Data

US 2015/0117607 A1    Apr. 30, 2015

(30) Foreign Application Priority Data

Oct. 25, 2013  (JP) ................................ 2013-221700

(51) Int. Cl.
| | |
|---|---|
| A61B 6/00 | (2006.01) |
| G06F 3/0484 | (2013.01) |
| G06F 3/0481 | (2013.01) |
| G06F 3/0482 | (2013.01) |

(52) U.S. Cl.
CPC .......... *G06F 3/04842* (2013.01); *A61B 6/463* (2013.01); *A61B 6/465* (2013.01); *A61B 6/5211* (2013.01); *A61B 6/5294* (2013.01); *A61B 6/563* (2013.01); *G06F 3/0482* (2013.01); *G06F 3/04817* (2013.01)

(58) Field of Classification Search
CPC ....... A61B 6/463; A61B 6/465; A61B 6/5294; A61B 6/4266
See application file for complete search history.

(56) References Cited

U.S. PATENT DOCUMENTS

| | | | |
|---|---|---|---|
| 2005/0259116 A1 | 11/2005 | Araoka | |
| 2013/0038738 A1* | 2/2013 | Ando | A61B 6/4266 348/162 |

FOREIGN PATENT DOCUMENTS

| | | |
|---|---|---|
| EP | 2491861 A1 | 8/2012 |
| EP | 2536161 A2 | 12/2012 |
| JP | 2000-166908 A | 6/2000 |

(Continued)

OTHER PUBLICATIONS

Extended European Search Report corresponding to Application No. 14187285.3-1660; Date of Mailing: Mar. 16, 2015.

(Continued)

*Primary Examiner* — Dani Fox
(74) *Attorney, Agent, or Firm* — Cantor Colburn LLP

(57) ABSTRACT

A console includes a display section. The console performs a focus display of the icon corresponding to the imaging order information regarding a currently-performed imaging, and when the imaging ends, moves the focus display of the icon to the icon of a next imaging. The console performs a focus display of the thumbnail image, and after a confirming process or when a predetermined time has passed, moves the focus display of the thumbnail image to a position at which the thumbnail image of the next imaging to be displayed on the display section. The console includes a first transition mode in which focus display transitions of the icon and thumbnail image are performed concurrently, and a second transition mode in which each of them is independently from each other. The transition mode of the focus display is capable of being switched between the first and second transition modes.

7 Claims, 16 Drawing Sheets

(56) References Cited

FOREIGN PATENT DOCUMENTS

JP     WO 2011142157 A1 * 11/2011 ........... A61B 6/4266
WO     2011/142157 A1    11/2011

OTHER PUBLICATIONS

Chinese Notification of the First Office Action corresponding to Application No. 201410573076.3; Date of Mailing: Aug. 17, 2016, with English translation.
Chinese Notification of Second Office Action corresponding to Application No. 201410573076.3; Date of Mailing: Mar. 9, 2017, with English translation.

* cited by examiner

FIG.9

| IMAGING ORDER ID | PATIENT ID | PATIENT NAME | SEX | AGE | HOSPITAL DEPARTMENT | IMAGING PORTION | IMAGING DIRECTION | BUCKY ID |
|---|---|---|---|---|---|---|---|---|
| 001 | 100085 | M | MALE | 25 | ORTHOPEDICS | CHEST | FRONT SIDE P → A | 002 |
| 002 | 100085 | M | MALE | 25 | ORTHOPEDICS | ABDOMEN | FRONT SIDE P → A | 001 |
| 003 | 100085 | M | MALE | 25 | ORTHOPEDICS | HEAD | FRONT SIDE P → A | 001 |
| 004 | 100085 | M | MALE | 25 | ORTHOPEDICS | LEG | R | 003 |
| 005 | 100063 | W | FEMALE | 32 | SURGERY | CHEST | LATERAL SIDE R → L | 001 |
| 006 | 100063 | W | FEMALE | 32 | SURGERY | ABDOMEN | FRONT SIDE A → P | 002 |

INPUT IMAGING ORDER INFORMATION FOR IMAGING TO BE PERFORMED.

| IMAGING ORDER ID | PATIENT ID | PATIENT NAME | SEX | AGE | HOSPITAL DEPARTMENT | IMAGING PORTION | IMAGING DIRECTION | BUCKY ID |
|---|---|---|---|---|---|---|---|---|
| 001 | 100085 | M | MALE | 25 | ORTHOPEDICS | CHEST | FRONT SIDE P→A | 002 |
| 002 | 100085 | M | MALE | 25 | ORTHOPEDICS | ABDOMEN | FRONT SIDE P→A | 001 |
| 003 | 100085 | M | MALE | 25 | ORTHOPEDICS | HEAD | FRONT SIDE P→A | 001 |
| 004 | 100085 | M | MALE | 25 | ORTHOPEDICS | LEG | R | 003 |

RETURN   ENTER

RADIOGRAPHIC IMAGE CAPTURING SYSTEM AND CONSOLE

CROSS REFERENCE

The present invention claims priority under 35 U.S.C. §119 to Japanese Application No. 2013-221700 filed Oct. 25, 2013, the entire content of which is incorporated herein by reference.

BACKGROUND OF THE INVENTION

Field of the Invention

The present invention relates to a radiographic image capturing system and a console, and especially to a console capable of displaying an icon corresponding to imaging order information, thumbnail image of a radiographic image, etc., and a radiographic image capturing system equipped with the console.

Description of Related Art

Heretofore, in a field of a radiographic image capturing system which irradiates an object with radiation such as an X-ray to capture a radiographic image for the purpose of disease diagnosis or the like, there has been increased a case of using a radiographic image capturing apparatus (Flat Panel Detector: FPD) in which radiation detecting elements, each converting irradiated radiation into electric charge, are arranged in the state of a two-dimensional matrix. The radiographic image capturing apparatus has been conventionally developed as a so-called exclusive machine integrally formed with a support and the like. However, a portable radiographic image capturing apparatus, which houses the radiation detecting elements and the like in a housing so as to be portable, is recently developed and comes into practical use.

To the radiographic image capturing system using such radiographic image capturing apparatus, a console is often introduced in order to control activation/operation of the radiographic image capturing apparatus and/or a radiation generator which emits radiation to the radiographic image capturing apparatus through an object. The radiographic image capturing system is often configured such that the console performs various correcting processes including offset correction, gain correction and defective pixel correction, and/or precise image processing including gradation correction depending on an imaging portion, with respect to image data and the like obtained by the radiographic image capturing apparatus, to generate the radiographic image to provide it for a diagnosis by a doctor, or the like.

For example, the inventions described in Japanese Patent Application Laid-open No. 2000-166908 and WO2011/142157 are examples of the invention having the configuration to generate the radiographic image based on image data and the like on the console. In each of the examples of the consoles described in Japanese Patent Application Laid-open No. 2000-166908 and WO2011/142157, when the image data and the like are transmitted to the console from the radiographic image capturing apparatus, the console automatically executes a generating process to generate the radiographic image on the basis of the image data and the like.

These documents also describe that the console displays icons corresponding to pieces of imaging order information regarding imaging performed by using the radiographic image capturing apparatus are displayed for the respective imaging orders, and displays, in a focused manner having a different mode from display modes of other icons, an icon corresponding to a piece of image order information regarding a currently-performed imaging or an imaging to be started.

Concretely, Japanese Patent Application Laid-open No. 2000-166908 describes displaying an arrow in the vicinity of the icon corresponding to the imaging order information regarding the currently-performed imaging or imaging to be started so that the icon is displayed in a focused manner. WO2011/142157 describes that the icon, which corresponds to the imaging order information regarding the currently-performed imaging or imaging to be started, is displayed in a focused manner by being colored with a color different from those of other icons. It is also described that the focus display of the icon moves to an icon corresponding to the next imaging every time imaging ends.

These patent documents also describe performing the imaging specified by the imaging order information corresponding to the icon displayed in the focused manner, and displaying the radiographic image and/or a preview image thereof, which have been generated based on the image data and the like transmitted to the console from the radiographic image capturing apparatus, at the positions where the icons have been displayed on the console.

Thus, by displaying the generated preview image and/or radiographic image at the display positions where the original icons corresponding thereto have been displayed, respectively, it becomes possible to inform an operator such as a radiologist that these images are generated based on the image data, which have been obtained by the imaging specified by the imaging order information corresponding to the icons. Also various beneficial effects can be further obtained. For example, the generated radiographic image can be definitely collated to the image order information, on the basis of which the radiographic image has been obtained.

By the way, an operator such as a radiologist often performs further adjusting processing (hereinafter simply referred to as an image quality adjusting process) of image quality etc., by executing fine adjustment of brightness/darkness or contrast with respect to the radiographic image which has been generated as described above and displayed on the console, though Japanese Patent Application Laid-open No. 2000-166908 and WO2011/142157 do not clearly describe that.

Incidentally, in such a case, the image which has been subjected to image quality adjustment is confirmed and correlated to the imaging order information. When the image quality and the like of the radiographic image generated by the console is appropriate, the image quality adjustment do not need to be executed again as a matter of course. For this reason, hereinafter, the phrase "to perform the image quality adjustment", etc. includes the case that an operator such as a radiologist judges that there is no need for the image quality adjustment and does not perform the image quality adjustment, as described above.

In the case of performing the image quality adjustment, for example, an operator accustomed to a work(s) can execute imaging of a plurality of radiographic images while successively changing the icon displayed in a focused manner, first, and then adjust image quality of each of the generated radiographic images in the order by which the operator can easily perform the processing, regardless of the order of imaging. If the radiographic image capturing system and/or the console are configured to allow the operator to freely do the works as described above, the operator accustomed to the works would get a feeling that the radiographic image capturing system and/or the console are easy to use.

On the other hand, as to an operator who is not accustomed to a work(s), if the radiographic image capturing system and/or the console are configured to allow the operator to perform imaging of all the radiographic images first and then execute the image quality adjustment of all the radiographic images at once, there may be occurred a problem that the operator becomes unable to understand which of the images has been or has not been subjected to the image quality adjustment. For this reason, the operator who is not accustomed to the works would feel safer if the radiographic image capturing system and/or the console are configured to allow the operator to execute the image quality adjustment every time the imaging is performed.

Concretely, the operator such as the radiologist executes the image quality adjustment of the radiographic image generated on the console when the imaging ends, and when the image quality adjustment is completed, performs next imaging and executes the image quality adjustment. If the radiographic image capturing system and/or the console configured to repeat such processing, the operator can execute the image quality adjustment at least every time the imaging is performed, and confirm the radiographic image to surely correlate the confirmed radiographic image to the imaging order information. Accordingly, it becomes possible to prevent the problem that the operator becomes unable to understand which of the images has been subjected to the image quality adjustment, and/or the problem that the operator forgets to execute the image quality adjustment, from occurring. Thus, the operator who is not accustomed to the works would feel safer if the radiographic image capturing system and/or the console have the above configuration.

Usability of the radiographic image capturing system and/or the console when separately executing the imaging and the image quality adjustment, or when executing the image quality adjustment after each imaging, may depend on not also whether or not the operator such as the radiologist is accustomed to the works as described above, but also a use mode of the radiographic image capturing system or the console.

Concretely, for example, even the operator accustomed to the works may wrongly perform the image quality adjustment to the radiographic image which has been taken by another operator and is displayed on the console, when the operator and the another operator share one (1) console, or may forget to perform the image quality adjustment in the misguided belief that the radiographic image has been taken by the another operator, though the radiographic image has been taken by the operator himself/herself. There may also be a case that the another operator wrongly performs the image quality adjustment to the radiographic image which has been taken by the operator himself/herself.

In such cases, it is preferable, even for the operator accustomed to the works, to configure the radiographic image capturing system and/or the console so that they perform the image quality adjustment for each imaging, because this does not allow the above-described misunderstanding of the operator, and enables the operator to execute the image quality adjustment of the radiographic image every time the imaging is performed, confirm the radiographic image, and surely correlate the radiographic image to the imaging order information.

As described above, the radiographic image capturing system and/or the console are required to be capable of accurately performing the image quality adjustment to the radiographic image, and surely correlating the radiographic image to the imaging order information, even when the operator such as the radiologist and/or the use mode of the radiographic image capturing system and/or the console change.

SUMMARY OF THE INVENTION

The present invention is made in view of the foregoing problems, and an object of the present invention is to provide a radiographic image capturing system and/or a console which are capable of accurately performing image quality adjustment to a radiographic image, and surely correlating the radiographic image to imaging order information, even when an operator such as a radiologist and/or a use mode of the radiographic image capturing system and/or the console change.

In order to achieve the above object, a radiographic image capturing system and/or a console of the present invention has the feature of including: a radiation generator which emits radiation to an object; a radiographic image capturing apparatus which includes a plurality of radiation detecting elements arranged in a two-dimensional state, and reads out, as the image data, electric charge occurring in the radiation detection elements upon radiation emission; and a console which resisters or obtains imaging order information regarding an imaging executed by using the radiographic image capturing apparatus, and generates a radiographic image based on image data transmitted from the radiographic image capturing apparatus, wherein the console includes a display section capable of displaying at least an icon corresponding to the imaging order information and a thumbnail image of the generated radiographic image, and wherein the console performs a focus display of the icon corresponding to the imaging order information regarding a currently-performed imaging, the focus display having a different mode from a display mode of another icon, and when the currently-performed imaging ends, moves the focus display of the icon to the icon corresponding to the imaging order information regarding a next imaging, wherein the console performs a focus display of the thumbnail image of the generated radiographic image, the focus display having a different mode from a display mode of another thumbnail image, and after a confirming process to the radiographic image or when a predetermined time has passed since the focus display has been performed, moves the focus display of the thumbnail image to a position, on the display section, at which the thumbnail image of the radiographic image generated based on the image data obtained by the next imaging is to be displayed, wherein the console includes, as a transition mode of the focus display, a first transition mode in which a transition of the focus display of the icon and a transition of the focus display of the thumbnail image are performed concurrently, and a second transition mode in which each of the transition of the focus display of the icon and the transition of the focus display of the thumbnail image is independently from each other, and wherein the transition mode of the focus display is capable of being switched between the first transition mode and the second transition mode.

According to the radiographic image capturing system and the console of the present invention, it becomes possible to surely correlate the radiographic image to the imaging order information, for example, by accurately performing the image quality adjustment to the radiographic image, even when an operator such as a radiologist to use the system and/or the console, or the use mode of the console, change. Accordingly, it becomes possible to accurately prevent the problem that the operator wrongly correlates the radiographic image to the imaging order information, and/or the problem that the operator wrongly confirms the radiographic image taken by another operator, in the misguided belief that the radiographic image has been taken by the operator himself/herself.

BRIEF DESCRIPTION OF THE DRAWINGS

The present invention will become more fully understood from the detailed description given hereinbelow and the appended drawings, and thus are not intended as a definition of the limits of the present invention, and wherein:

FIG. 9 is a diagram illustrating examples of pieces of imaging order information;

FIG. 10 is a diagram illustrating an example of a selection screen displaying pieces of the imaging order information;

PREFERRED EMBODIMENT OF THE PRESENT INVENTION

Hereinafter, embodiments of a radiographic image capturing system and a console according to the present invention will be described with reference to the drawings.

Incidentally, as a radiographic image capturing apparatus used in the radiographic image capturing system, a radiographic image capturing apparatus of so-called indirect type which is equipped with a scintillator or the like and converts irradiated radiation into light of other wavelengths such as visible light to obtain an electrical signal will be described. However, the present invention can also be applied to a radiographic image capturing apparatus of so-called direct type, which directly detects radiation with radiation detecting elements, without the scintillator or the like.

Moreover, a case that the radiographic image capturing apparatus is a so-called portable type will be described, but the present invention can be applied to a so-called exclusive-machine type (also called as an installed type) radiographic image capturing apparatus. The present invention is not limited to ones illustrated below.

Figure 1:
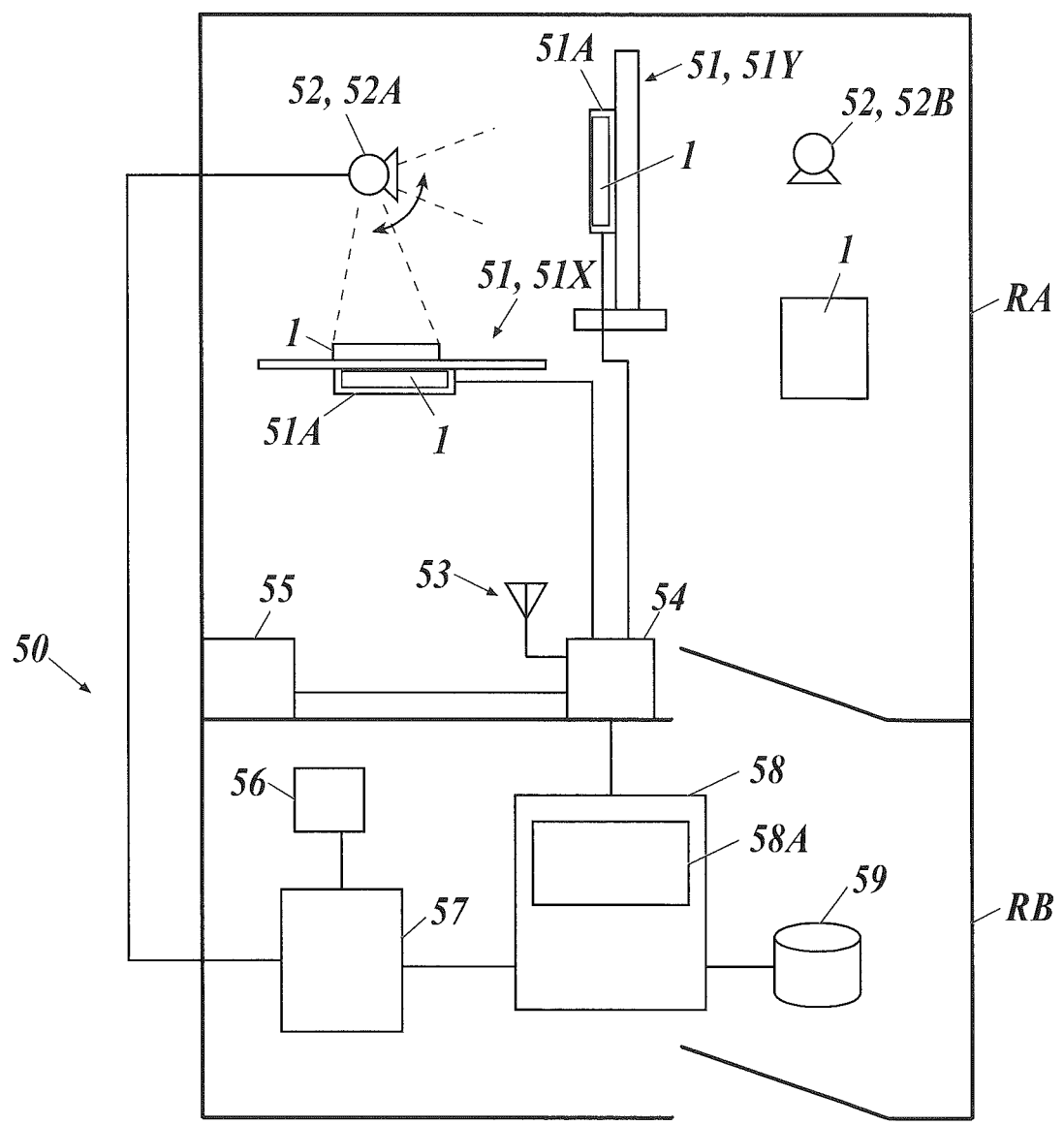
FIG. 1 is a diagram illustrating an overall configuration of a radiographic image capturing system according to this embodiment.

FIG. 1 is a diagram illustrating a basic configuration of the radiographic image capturing system according to this embodiment. Here, a radiographic image capturing system 50 in which an imaging room RA and a console 58 are correlated to each other on a one-to-one basis is illustrated to explain the basic configuration of the radiographic image capturing system 50 of the embodiment. Incidentally, a case that the imaging room(s) RA and the console(s) 58 are correlated to each other in a mode other than the one-to-one basis will be described later.

The imaging room RA is a room where an object (i.e. an imaging portion of a patient) as a part of a body of the patient is irradiated with radiation to capture a radiographic image. In the imaging room RA, a radiation source 52 of a radiation generator 57 emitting the radiation to the object, and the like, are disposed. Incidentally, the imaging room RA is sealed with lead and the like so that the radiation does not leak outside the room.

[Regarding Radiographic Image Capturing Apparatus]

Figure 2:
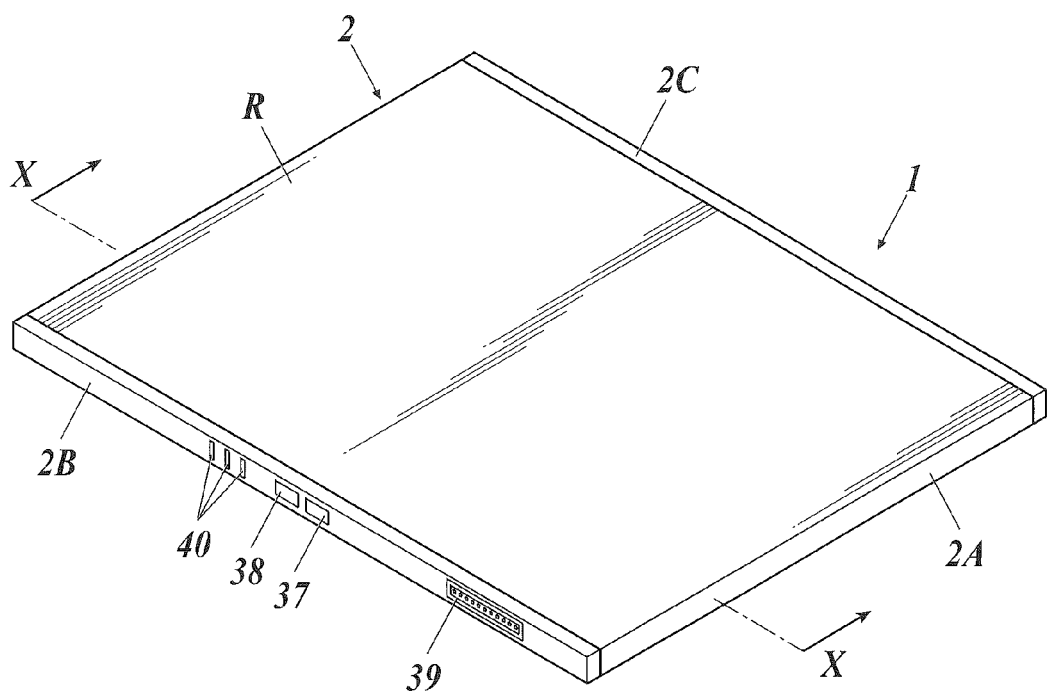
FIG. 2 is a perspective view of an appearance of a radiographic image capturing apparatus.
Figure 3:
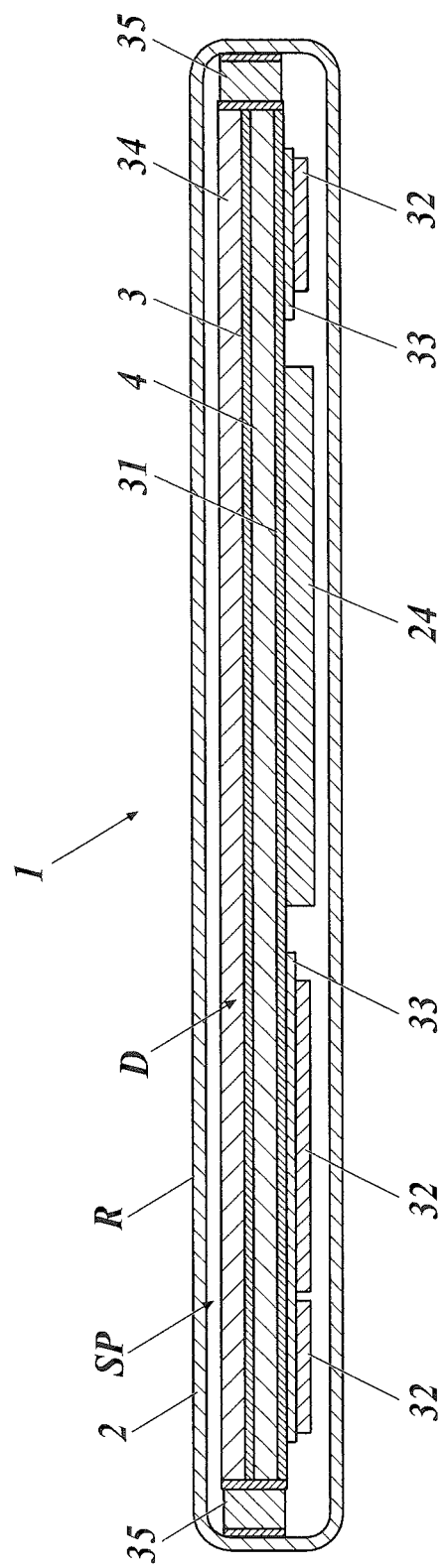
FIG. 3 is a cross-sectional view along X-X line in FIG. 2.

Here, a radiographic image capturing apparatus 1 used to capture the radiographic image in the radiographic image capturing system 50 will be described. FIG. 2 is a perspective view of an appearance of the radiographic image capturing apparatus, and FIG. 3 is a cross-sectional view along X-X line in FIG. 2. Incidentally, in the drawings such as FIG. 2 and FIG. 3, actual relative sizes of sections/portions are not always reflected in the relative sizes of illustrated sections/portions.

As illustrated in FIG. 2 and FIG. 3, the radiographic image capturing apparatus 1 is configured such that a sensor panel SP is housed in a housing 2 including a radiation incident surface R, the sensor panel SP being composed of a scintillator 3, a sensor substrate 4, etc. In a lid member 2B on one side of the housing 2, a power switch 37, a selection switch 38, a connector 39, an indicator 40 which is composed of LEDs and the like and displays a buttery condition, an operation condition of the radiographic image capturing apparatus 1, etc. and so on are disposed.

In a lid member 2C on the opposite side of the housing 2, an antenna device 41 (see FIG. 5 to be described later) as a communication member, which wirelessly transmits image data and the like to a later-described console 58 (see FIG. 1), is provided by being embedded therein, or by other means. Incidentally, there may be adopted a configuration where a not-illustrated cable is attached to the connector 39 so that the image data and the like are transmitted to the console 58 in a wire system.

As illustrated in FIG. 3, a base 31 is disposed in the housing 3, and the sensor substrate 4 is disposed on a radiation-incident-surface R side (hereinafter simply referred to as an upper-surface side, etc., in conformity to a vertical direction in the drawings) of the base 31 through a not-illustrated lead thin film or the like. Additionally, a scintillator substrate 34 is provided so that the scintillator 3 which converts the irradiated radiation into light such as visible light is disposed on the upper-surface side of the sensor substrate 4.

On a lower surface side of the base 31, there are disposed a PCB substrate 33 on which electronic components 32 and the like are arranged, a battery 24, and so on. The sensor panel SP is thus composed of the base 31, the sensor substrate 4, and so on. Furthermore, in the embodiment, a cushioning 35 is provided between the sensor panel SP and each of the sides of the housing 2.

Figure 4:
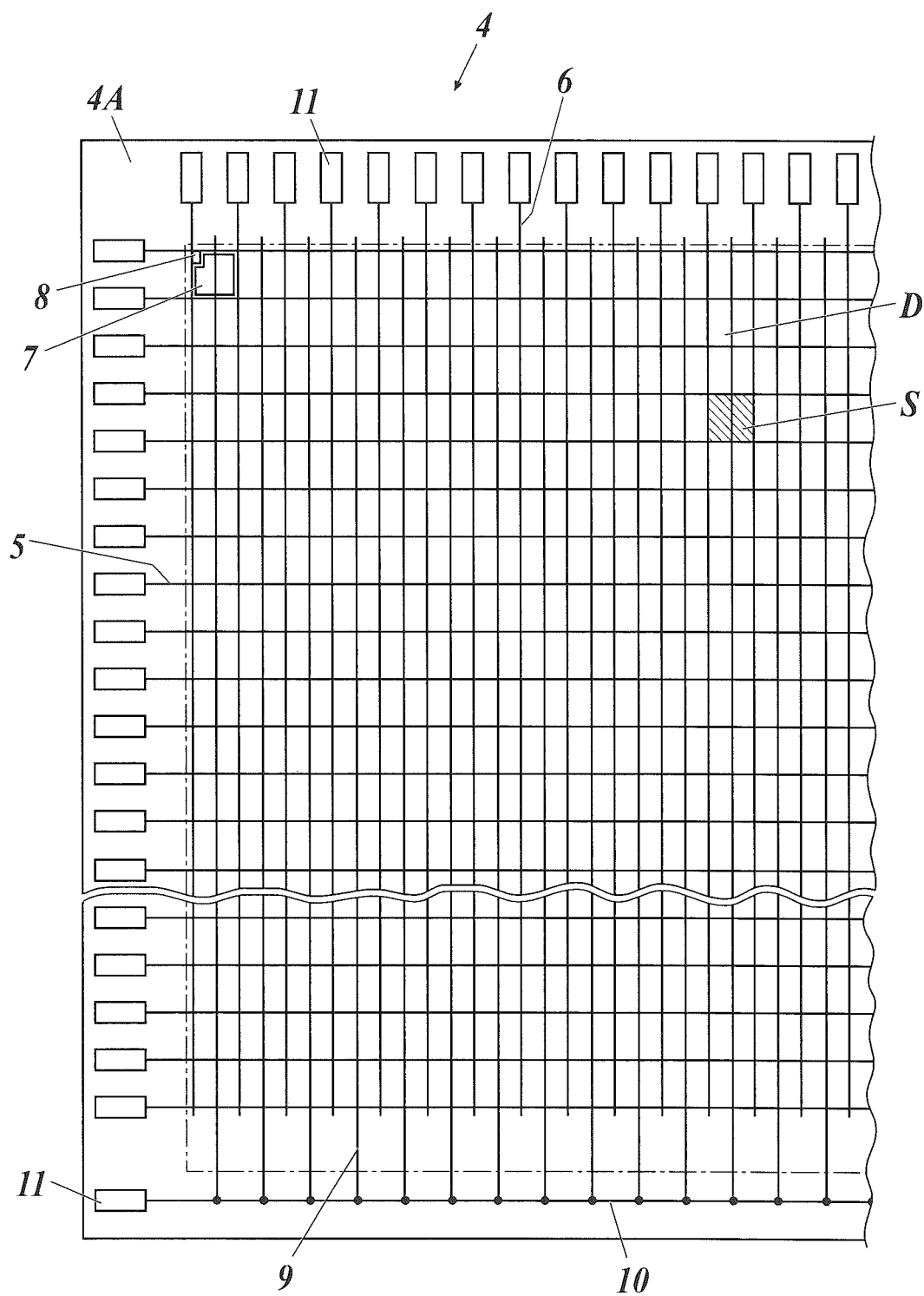
FIG. 4 is a plain view illustrating a configuration of a sensor substrate of the radiographic image capturing apparatus.

The sensor substrate 4 of the embodiment is composed of a glass substrate, and as illustrated in FIG. 4, a plurality of scanning lines 5 and a plurality of signal lines 6 are arranged so as to cross each other on a surface 4A of the sensor substrate 4, the surface 4A facing the scintillator 3. In small areas S divided by the scanning lines 5 and the signal lines 6 on the surface 4A of the sensor substrate 4, a plurality of radiation detecting elements 7 are disposed, respectively.

Thus, the radiographic image capturing apparatus 1 of the embodiment is equipped with the plurality of radiation detecting elements 7 arranged in a two-dimensional state. In the embodiment, photodiodes are used as the radiation detecting elements 7. However, for example, also phototransistors or the like may be used. Each of the radiation detecting elements 7 generates an electric charge in the inside thereof depending on an amount of the irradiated radiation, which is the visible light obtained by convering the irradiated radiation in the scintillator 3 in the case of the embodiment.

To each of the radiation detecting elements 7, a Thin Film Transistor (hereinafter referred to as a TFT) 8 is connected. The TFT is a switch element which becomes an ON state and discharges the electric charge in each of the radiation detecting elements 7 to each of the signal lines 6 when an ON voltage is applied to each of the scanning lines 5, and becomes an OFF state and makes the electric charge, which has been generated in each of the radiation detecting elements 7, accumulated in each of the radiation detecting elements 7, when an OFF voltage is applied to each of the scanning lines 5.

Each of the signal lines 6 is connected to each reading circuit in a not-illustrated reading IC. In a reading process of image data D, the electric charge discharged to each of the signal lines 6 through the TFT 8, which has become the ON state as described above, flows into the reading circuit, and converted into the image data D in the reading circuit. Thus, the electric charge, which has been generated upon irradiation of radiation in each of the radiation detecting elements 7 of the radiographic image capturing apparatus 1, is read out as the image data D for each of the radiation detecting elements 7.

Incidentally, in the embodiment, an area D in which the radiation detecting elements 7 are arranged in the two-dimensional state is defined as a detecting section. To each of the radiation detecting elements 7, a reverse bias voltage is applied via each of bias lines 9, and the bias lines 9 are connected to a tie line 10, as illustrated in FIG. 4. Each of the scanning lines 5, the signal lines 6, the tie line 10 of the bias lines 9, and the like is connected to an input/output terminal 11, and is connected to a not-illustrated flexible circuit substrate and the like, and further to the above-described electronic components 32 and/or the reading IC, through the input/output terminal 11.

In the embodiment, the radiographic image capturing apparatus 1 reads out the image data D from the radiation detecting elements 7 as described above to store the image data D in a not-illustrated storage member, and extracts a piece of or pieces of image data DP from the image data D at a constant rate to transmit the extracted image data DP for preview image to the console 58.

At the same time of transmitting the image data DP for preview image, the radiographic image capturing apparatus 1 also repeatedly performs a processing sequence same as the processing sequence up to the reading process of the image data D in the state that the radiation is not emitted, so as to perform a reading process of offset data O, in which the offset data O due to a dark electric charge (also referred to as a dark current, etc.) accumulated in the radiation detecting elements 7 is read out from each of the radiation detecting elements 7.

When the reading process of the offset data O has been performed, the radiographic image capturing apparatus 1 of the embodiment then transmits the remaining image data D other than the image data DP for preview image, and the read-out offset data O, to the console 58.

Incidentally, in the embodiment, when the radiographic image capturing apparatus 1 is loaded into a Bucky device 51 as described later, the image data DP for preview image, image data D, the offset data O, etc. are transmitted to the console 58 via a connector 51B (see FIG. 5 and FIG. 6) of the Bucky device 51, which is connected to the connector 39, in the wire system.

In the case that the radiographic image capturing apparatus 1 is not loaded into the Bucky device 51 and is used independently, the image data DP for preview image and the like are wirelessly transmitted to the console 58 via the above-described antenna device 41. The order of transmission is not limited to the above-described order.

[Regarding Other Apparatuses/Devices, Etc. In Radiographic Image Capturing System]

Next, the apparatuses/devices in the radiographic image capturing system 50 will be described. As illustrated in FIG. 1, the Bucky device 51 of the embodiment is capable of being used in the state that the portable radiographic image capturing apparatus 1 is loaded into a cassette holding section (also referred to as a cassette holder) 51A.

In the embodiment, as illustrated in FIG. 1, there are disposed a Bucky device 51Y for standing position imaging and a Bucky device 51X for lying position imaging, as the Bucky devices 51, in the imaging room RA. Alternatively, for example, the present invention may be applied to a case where only the Bucky device 51Y for standing position imaging is disposed, or a case where only the Bucky device 51X for lying position imaging is disposed.

Each of the Bucky devices 51 of the embodiment is configured to be also capable of being used in the state that a conventional CR cassette is loaded into the cassette holding section 51A, and an existing Bucky device installed for the CR cassette in the imaging room RA may be used.

For this reason, in the embodiment, the above-described radiographic image capturing apparatus 1 is configured to have the same size as the CR cassette. Concretely, the CR cassette is formed so as to have a certain size such as 14 inch×17 inch (size of paper cut in half) in conformity to a JIS standard size of a conventional screen film cassette, the JIS standard corresponding to the international standard, IEC 60406. The CR cassette is also formed so as to have a thickness, in a radiation incident direction, in a range from 13 mm to 16 mm.

In the embodiment, in order to enable the radiographic image capturing apparatus 1 to be loaded into the Bucky device 51, to which the CR cassette having the JIS standard size can be loaded, also the radiographic image capturing apparatus 1 is formed so as to have a certain size in conformity to the JIS standard of the screen film cassette, similarly to the CR cassette in conformity to the JIS standard. Incidentally, the present invention is not limited to the case where the Bucky device for CR cassette is used as the Bucky device 51.

Figure 5:
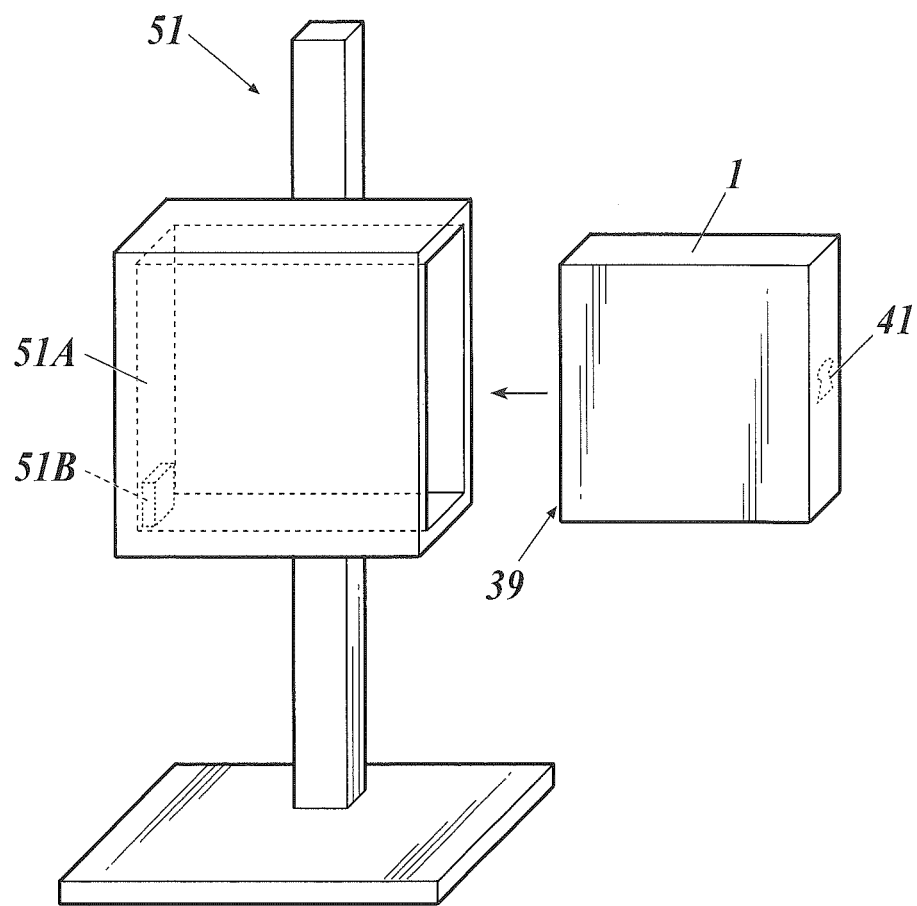
FIG. 5 is a diagram for explaining about a Bucky device in which a connector is housed in a cassette holding section.

Moreover, the connector 51B, which is to be automatically connected to the connector 39 (see FIG. 2) of the loaded radiographic image capturing apparatus 1, may be disposed, for example, in the inside of the cassette holding section 51A of the Bucky device 51. Although FIG. 5 illustrates the case of the Bucky device 51Y for standing position imaging, the same can be said for the case of the Bucky device 51X for lying position imaging.

Figure 6:
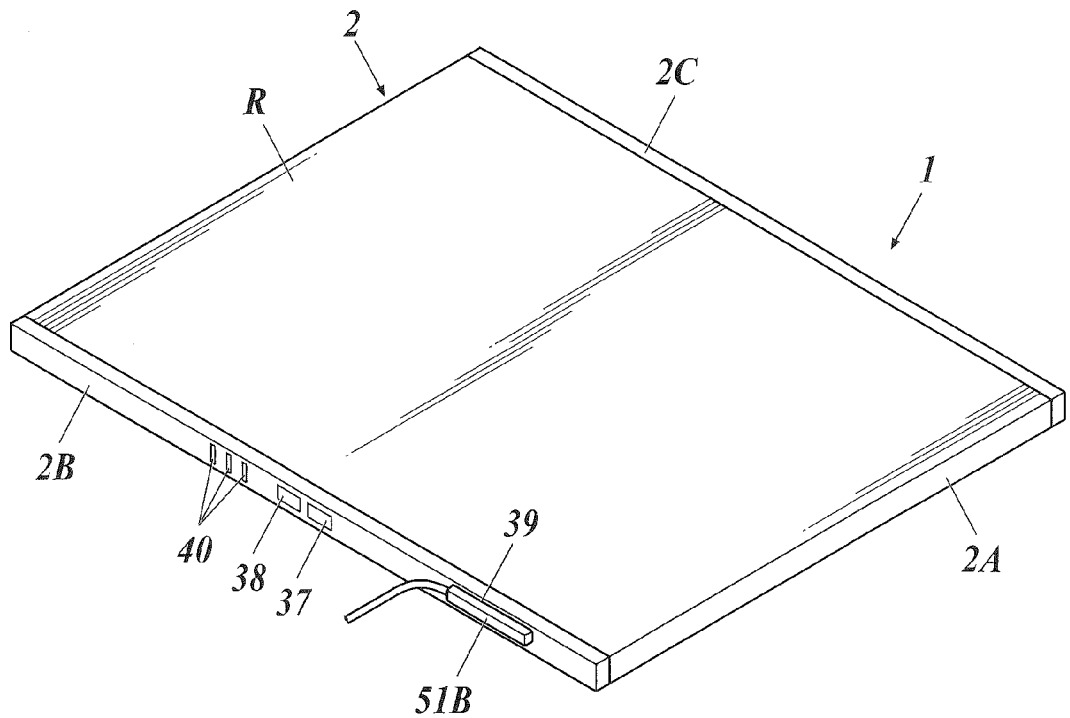
FIG. 6 is a perspective view of an appearance illustrating a state that a connector of the radiographic image capturing apparatus and the connector of the Bucky device are connected to each other.

It is also possible, as illustrated in FIG. 6, to connect the connector 51B, which is at a tip of a cable extending from the Bucky device 51, to the connector 39 of the radiographic image capturing apparatus 1 before loading the radiographic image capturing apparatus 1 into the Bucky device 51, and in this state, to load the radiographic image capturing apparatus 1 into the cassette holding section 51A of the Bucky device 51.

In the case of configuring the radiographic image capturing apparatus 1 and the Bucky device 51 so that they are connected to each other as illustrated in FIG. 6 when loading the radiographic image capturing apparatus 1 into the Bucky device 51, the radiographic image capturing apparatus 1 may be configured so as to receive a power supply from the Bucky device 51. In the case of using the radiographic image capturing apparatus 1 independently, namely, in the state of not being loaded into the Bucky device 51, the battery 24 (see FIG. 3) supplies power to each functional section of the radiographic image capturing apparatus 1.

In the embodiment, when the connector 51B (see FIG. 5 or FIG. 6) of the Bucky device 51 and the connector 39 of the radiographic image capturing apparatus 1 are connected to each other, the Bucky device 51 reads out a cassette ID, which is identification information of the radiographic image capturing apparatus 1, from the radiographic image capturing apparatus 1, and correlates the cassette ID of the radiographic image capturing apparatus 1 to a Bucky ID which is identification information of the Bucky device 51 itself to transmits those to the console 58.

As illustrated in FIG. 1, there is provided at least one (1) radiation source 52 of the radiation generator 57, which emits the radiation to an object, in the imaging room RA. In the embodiment, among the radiation sources 52, one (1) radiation source 52A is disposed, for example, by being suspended from a ceiling of the imaging room RA, and at the time of imaging, the radiation source 52A is activated based on an instruction from the console 58 and is moved to a predetermined position by a not-illustrated moving member.

It is possible to adopt the configuration enabling changing the radiation irradiation direction and/or the position of the radiation source 52 so that one (1) radiation source 52 can emit the radiation to the radiographic image capturing apparatus 1 loaded into the Bucky device 51Y for standing position imaging or loaded into the Bucky device 51X for lying position imaging. Alternatively, it is also possible to dispose the radiation sources 52 in the Bucky device 51Y for standing position imaging and the Bucky device 51X for lying position imaging, respectively.

Furthermore, as illustrated in FIG. 1, it is possible to bring a portable radiation source 52B, which is not correlated to the Bucky device 51Y for standing position imaging or the Bucky device 51X for lying position imaging, to perform the imaging. At that time, the portable radiation source 52B can be carried to an arbitrary position in the imaging room RA, and can emit the radiation in an arbitrary direction.

By using the portable radiation source 52B, the radiation can be emitted from a proper distance and/or in a proper direction while putting the radiographic image capturing apparatus 1 on a body portion of a patient as an object, or while inserting the radiographic image capturing apparatus 1 between a patient body and a top panel of the Bucky device 51X for lying position imaging and/or a not-illustrated bed, in an independent state (in the state of not being loaded into the Bucky device 51).

Because the imaging room RA is sealed with lead or the like as described above, the information such as the image data D cannot be transmitted/received as it is, even when trying to transmit/receive such information from/with the radiographic image capturing apparatus 1 via the antenna device 41, in the imaging room RA. For this reason, in the embodiment, as illustrated in FIG. 1, there is disposed in the imaging room RA a repeater (also referred to as a base station, etc.) 54 equipped with an access point 53 to relay wire or wireless communication when the apparatuses/devices in the imaging room RA, such as the radiographic image capturing apparatus 1, communicate with apparatuses/devices outside the imaging room RA, such as the console 58, in a wire or wireless system.

The repeater 54 includes therein a not-illustrated convertor which converts signals and the like used for Local Area Network (LAN) communication for transmission from the radiographic image capturing apparatus 1 and/or the console, etc. to the radiation generator 57, into the signals and the like for the radiation generator 57, and vice versa.

Figure 7:
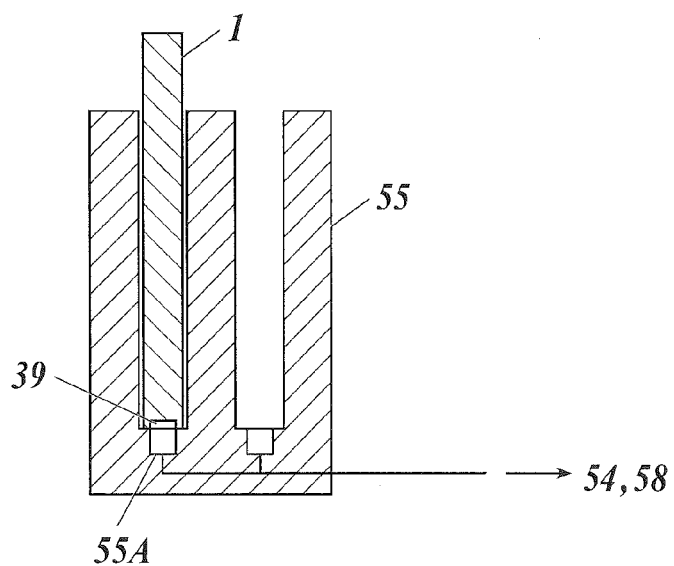
FIG. 7 is a cross-sectional view illustrating a state that the radiographic image capturing apparatus is inserted into a cradle, and connecters thereof are connected to each other.

Also a cradle 55 is connected to the repeater 54 of the embodiment. As illustrated in FIG. 7, when the radiographic image capturing apparatus 1 is brought into the imaging room RA and inserted into the cradle 55, and when the connector 39 of the radiographic image capturing apparatus 1 and a connector 55A of the cradle 55 are connected to each other, the cassette ID is reported to the repeater 54 from the radiographic image capturing apparatus 1 through the cradle 55. When the cassette ID of the radiographic image capturing apparatus 1 is transmitted to the repeater 54 from the cradle 55, the repeater 54 informs the console 58 of the cassette ID.

Incidentally, the cradle 55 is generally used to house and/or charge the radiographic image capturing apparatus 1 or the like. Also in the embodiment, the cradle 55 may be configured so as to have a charging function and the like. Moreover, though FIG. 7 illustrates the cradle 5 having two insertion holes into which the radiographic image capturing apparatus 1 may be inserted, but there may be one (1) insertion hole, or three or more insertion holes.

The cradle 55 may be disposed in either of the imaging room RA and a front room RB. In the case that the cradle 55 is disposed in the imaging room RA, the cradle 55 is disposed at a position at which the radiation emitted from the radiation generator 52 does not arrive, for example, at a corner position of the imaging room RA.

Figure 8:
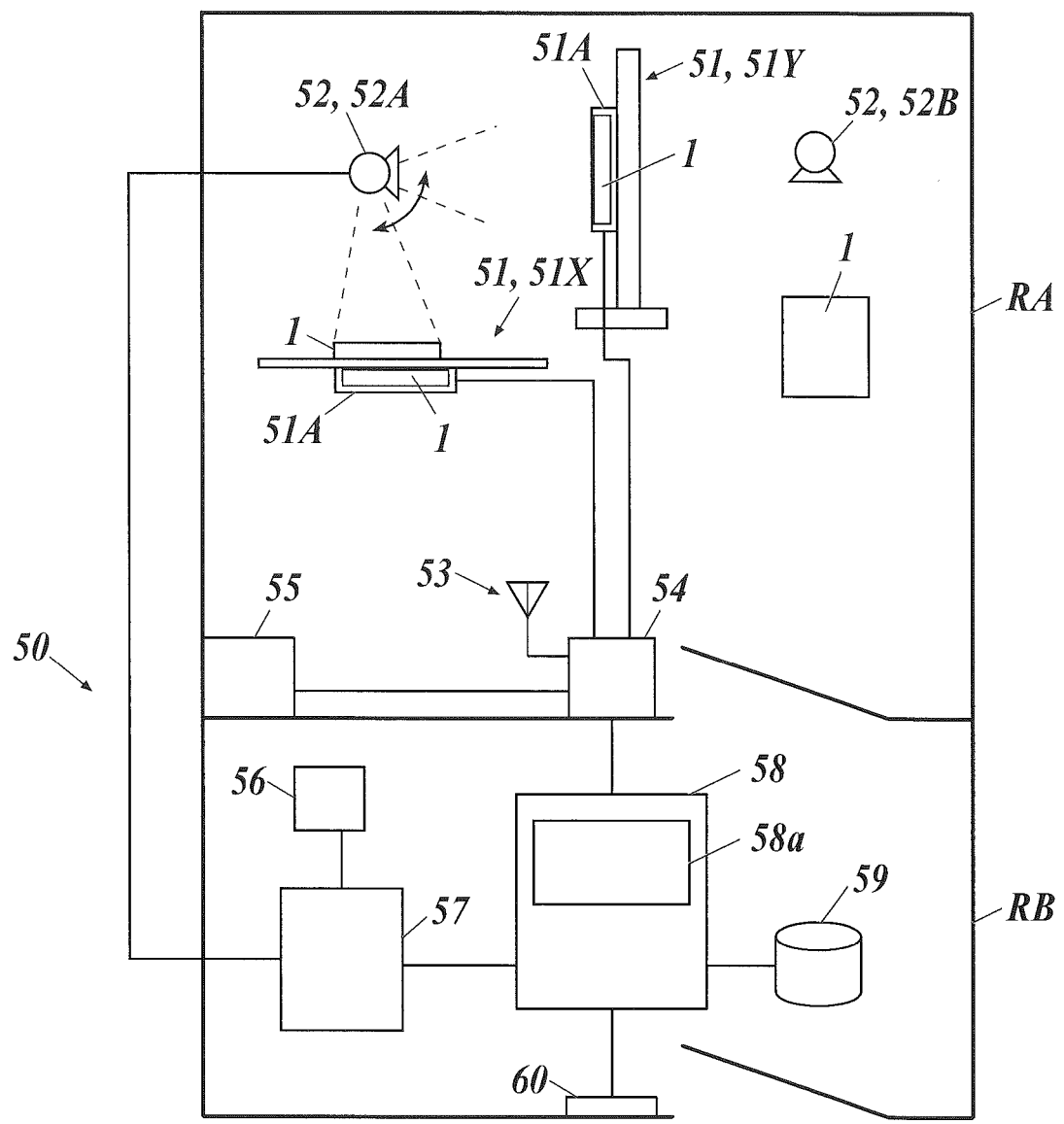
FIG. 8 is a diagram illustrating a configuration to include a tag reader as a detecting section.

It is also possible to dispose a tag reader 60, for example, in the vicinity of a door of the front room RB as illustrated in FIG. 8, as a detecting member to detect the radiographic image capturing apparatus 1 brought into the imaging room RA and/or the front room RB to report the cassette ID to the console 58, instead of using the cradle 55 as the embodiment.

In this case, a not-illustrated tag such as a so-called Radio Frequency IDentification (RFID) tag is previously contained in the radiographic image capturing apparatus 1, the tag previously storing specific information such as the cassette ID of the radiographic image capturing apparatus 1. When the radiographic image capturing apparatus 1 passes in the vicinity of the tag reader 60 to be brought into the imaging room RA and/or the front room RB, the tag reader 60 may read the information such as the cassette ID from the tag of the radiographic image capturing apparatus 1 to report the cassette ID to the console 58.

As illustrated in FIG. 1, there is disposed, in the front room RB (also referred to as a control room, etc.), the radiation generator 57 equipped with an exposure switch 56 to instruct the radiation source 52 to start radiation emission, etc. When a tube voltage, tube current, irradiation time, etc. are set, the radiation generator 57 applies the set tube voltage and/or tube current to the radiation source 52 to activate the same so that the radiation source 52 emits the radiation of dose corresponding to the set tube voltage or the like, for the set irradiation time.

Incidentally, setting of the tube voltage and the like to the radiation generator 57 may be performed on an operator station 57. In the embodiment, such setting may be performed also on the console 58.

The console 58 is disposed in the front room RB in the embodiment, and is composed of a not-illustrated Central Processing Unit (CPU), Read Only Memory (ROM), Random Access Memory (RAM), a computer including an input/output interface, etc. connected to a bus, and so on. The ROM stores predetermined programs. The console 58 reads out a necessary program to expand it in a work area of the RAM, and executes various processes according to the program. Incidentally, the console 58 does not always need to be composed of a general-purpose computer, and may be composed of, for example, a dedicated device.

The console 58 is equipped with a display section 58A which is composed of a Cathode Ray Tube (CRT), a Liquid Crystal Display (LDC), and so on. To the console 58, a not-illustrated input member such as a keyboard and a mouse, etc. are connected. Also a storage member 59 composed of a hard disk and the like is connected to the console 58. Additionally, other computers, and/or external devices such as an imager which records the radiographic image based on the image data output from the console 58 in an image recording medium such as a film and outputs the radiographic image, are connected to the console 58 via an LAN or the like.

When the radiographic image capturing apparatus 1 is brought into the imaging room RA and inserted as described above, and when the cassette ID and the like of the radiographic image capturing apparatus 1 is transmitted to the console 58 from the cradle 55 or the tag reader 60 via the repeater 54, the console 58 stores the cassette ID in the storage member 59, and recognizes/manages the fact that the radiographic image capturing apparatus 1 having the cassette ID has been brought into the imaging room RA or the front room RB, as described above.

Moreover, when the cassette ID of the radiographic image capturing apparatus 1 and the Bucky ID are transmitted from the Bucky device 51 including the connector 51B to which the radiographic image capturing apparatus 1 is connected, the console 58 correlates the Bucky ID to the cassette ID stored in the storage member 59 to store them together.

When the connection between the radiographic image capturing apparatus 1 and the connector 51B of the Bucky device 51 is released, the correlation between the cassette ID of the radiographic image capturing apparatus 1 and the Bucky ID, which are stored in the storage member 59, is released, and only the cassette ID is stored.

Thus, the console 58 recognizes/manages whether or not the radiographic image capturing apparatus 1 is loaded into the Bucky device 51, which of the radiographic image capturing apparatuses 1 is loaded into the Bucky device 51, and to which of the Bucky devices 51 the radiographic image capturing apparatuses 1 is loaded, when the radiographic image capturing apparatus 1 is loaded into the Bucky device 51 to be used. When the CR cassette has been loaded into the Bucky device 51, the console 58 reads a bar cord attached to the CR cassette to recognize/manage which of the CR cassettes is loaded into the Bucky device 51, and to which of the Bucky devices 51 the CR cassettes is loaded.

To the console 58, a not-illustrated Hospital Information System (HIS) and/or a Radiology Information System (RIS) are connected via a network. In the HIS, patient information is registered. In the RIS, imaging order information, in which information necessary for capturing a predetermined radiographic image for an individual patient is previously set, is registered.

The imaging order information is composed of, as illustrated in FIGS. 9 and 10, a "Patient ID" P2, "Patient Name" P3, "Sex" P4, "Age" P5 and "Hospital Department" P6 as the patient information, and an "Imaging Portion" P7 and "Imaging Direction" P8 as imaging conditions, and so on. Additionally, in the embodiment, a column of "Bucky ID" P9 is provided as information indicating whether or not imaging is performed in the state that the radiographic image capturing apparatus 1 is loaded into the Bucky device 51. The Bucky IDs are described in the column of P9 when the radiographic image capturing apparatus 1 is loaded into the Bucky device 51.

In the example illustrated in FIG. 9, the Bucky IDs "001" and "002" indicate the Bucky device 51Y for standing position imaging and the Bucky device 51X for lying position imaging, respectively, and the Bucky ID "003" indicates that the radiographic image capturing apparatus 1 is used independently without being loaded into the Bucky device 51. Incidentally, instead of the Bucky IDs, for example, it is possible to describe design/drawing patterns representing the Bucky device 51Y for standing position imaging, the Bucky device 51X for lying position imaging, and/or the radiographic image capturing apparatus 1 alone, respectively in the column of P9 of the imaging order information, so that they can be immediately grasped at a glance.

To respective pieces of the imaging order information, "Imaging Order IDs" P1 are automatically allocated, in the order of registration of imaging orders. Incidentally, the contents of the patient information and/or the imaging condition written in the imaging order information are not limited to the above contents. For example, the imaging order information may include other information such as a birth date of a patient, a frequency of medical examination, a radiation dose and information about whether a patient is fat or thin.

The console 58 obtains necessary imaging order information and the like from the RIS and/or HIS, by operation of the operator such as the radiologist, when the imaging order information and the like have been registered in the RIS and/or HIS. Incidentally, the imaging order information may be registered/input in the console 58 itself by using a dedicated terminal, not in the RIS and/or HIS. In this case, the console 58 obtains the imaging order information from the storage member 59 in which the imaging order information has been registered/input and stored.

When the console 58 obtains the imaging order information, the console 58 displays a list of pieces of the imaging order information as a selection screen H1 in the display section 58A of the console 8, as illustrated in FIG. 10. Hereinafter the case of displaying a plurality of pieces of imaging order information relating to one (1) patient will be described.

In the embodiment, the selection screen H1 includes an imaging order information display field H11 in which the list of pieces of the imaging order information is displayed, and selection buttons H12 for selecting each piece of the imaging order information for the imaging to be performed are disposed near the left side of the imaging order information display field H11, correspondingly to the respective pieces of the imaging order information. Additionally, there are provided an enter button H13 and a return button H14 below the imaging order information display field H11.

Figure 11:
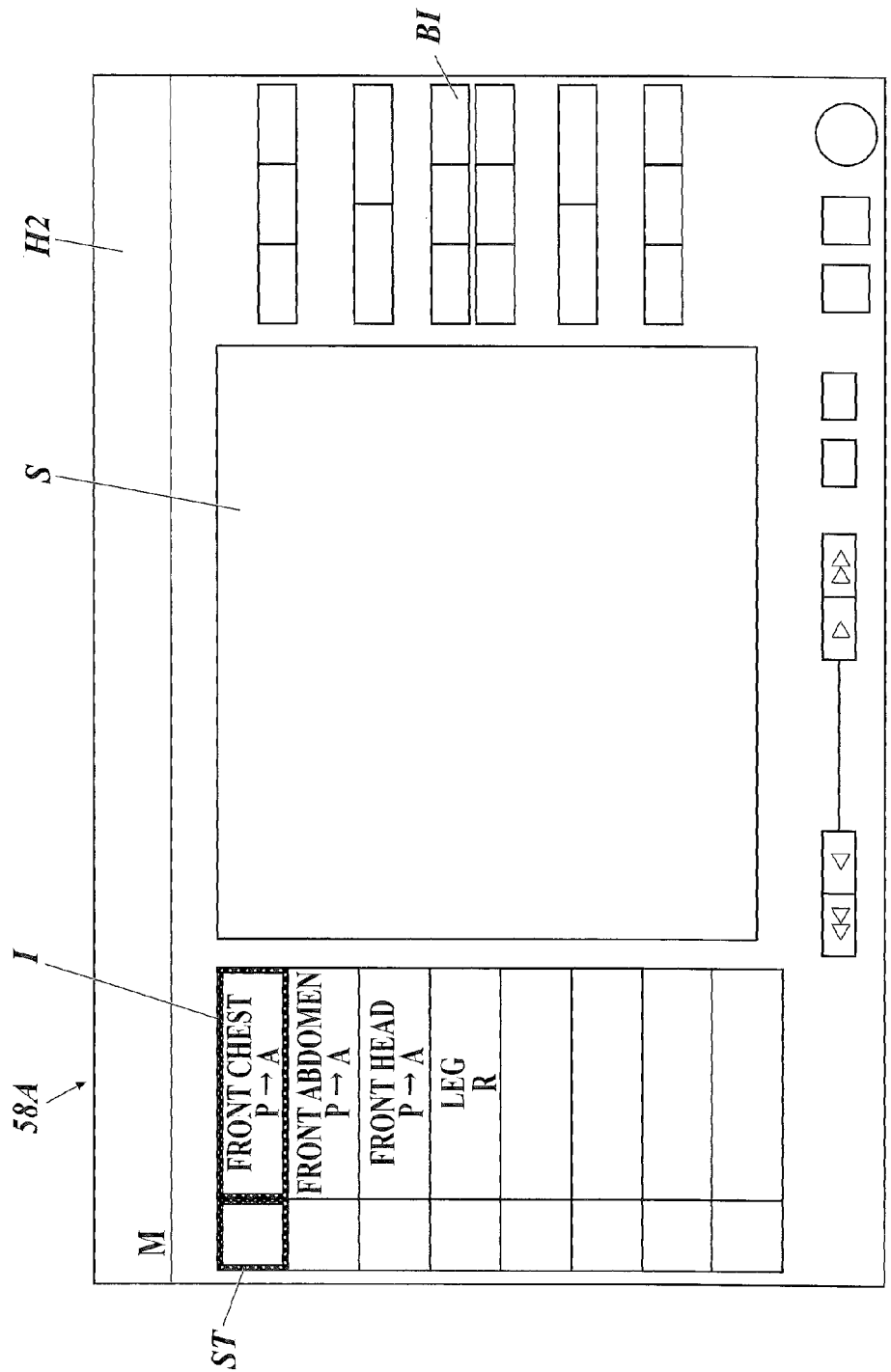
FIG. 11 is a diagram illustrating an example of a screen displaying icons corresponding to pieces of the imaging order information, respectively.

The console 58 of the embodiment displays, for example, the screen H2 in the display section 58A as illustrated in FIG. 11, when the operator such as the radiologist clicks the selection buttons H12 to select all of the four pieces of the imaging order information, and then clicks the enter button H13.

In this case, there is provided, in the center of the screen H2, a display working space S in which a preview image P_PRE, a radiographic image P, etc. generated by the console 58 are displayed. On the right-hand side of the screen H2, there are provided various button icons BI which enables then operator such as the radiologist to adjust an image quality of the radiographic image P generated by the console 58 by finely adjusting brightness/darkness, contrast, and the like of the image, namely, to perform the above-described image quality adjusting process to the radiographic image P generated by the console 58.

Incidentally, in the embodiment, the button icons BI are displayed only when the display working space S is valid, namely, displayed. Alternatively, also a configuration where the button icons BI are always displayed but the operations to the button icons BI become effective only when the display working space is valid may be adopted.

On the left-hand side of the screen H2, icons corresponding to respective pieces of the imaging order information selected on the selection screen H1 (see FIG. 10) are displayed, for example, in the state of being arranged in a longitudinal direction. In the embodiment, the imaging conditions such as the "Imaging Portion" P7 and "Imaging Direction" P8 (see FIG. 10, etc.) of pieces of the imaging order information, which correspond to the icons I respectively, are described in the respective icons I. Although FIG. 11 illustrates the example where the icons I are arranged in the order of the "Imaging Order IDs" P1 (see FIG. 10, etc.), namely in the order of registration, the icons I may be arranged in another order. The present invention is also not limited to the case that the icons I are displayed while being arranged in the longitudinal direction, and a way of displaying the icons I may be arbitrary determined.

At positions adjacent to the icons I, respectively, or in the inside of the icons I, there are provided spaces ST in which the preview images P_PRE generated based on the image data D and/or the image data DP for preview image obtained by the imaging based on the imaging order information corresponding to the icons I, and/or thumbnail images PT are displayed.

The console 58 displays the icon(s) I corresponding to piece or pieces of the imaging order information relating to the currently-executed imaging in a focused manner having a different mode from display modes of other icons I. Specifically, in the embodiment, the icon I is displayed in the focused manner by being enclosed with a frame, as illustrated in FIG. 11. Incidentally, though the focus display is performed by displaying the frame with a black color in FIG. 11, actually, the whole of the screen H2 and/or the icon I are often displayed with a black color or dark gray. In such a case, the focus display is executed by enclosing the icon I with a frame of bright color, and thereby the operator such as the radiologist can easily and accurately recognize the focused icon I.

Incidentally, the way of executing the focus display is not limited to enclosing the icon I with the frame as described above. For example, as described above, also displaying the icon I while coloring it with a color different from those of other icons I, making the focused icon I blink on and off, changing a display position of the focused icon I on the screen H2, or zooming-up and displaying may be adopted. Thus, the focus display is not limited to the specific means.

When the currently-executed imaging ends, the console 58 makes the focus display of the icon I move from the icon I corresponding to the imaging order information relating to the imaging which has been executed until then, to the icon I (hereinafter simply referred to as the icon I of a next imaging) corresponding to the imaging order information relating to the next imaging.

In this case, for example, it is also possible to make the focus display of the icon I move in the order of registration of pieces of the imaging order information, namely, in the order of the "Imaging Order IDs" P1 (see FIG. 10, etc.). The console 58 of the embodiment performs the transition of the focus display of the icon I by the way described in the above-described WO2011/142157. Concretely, the console 58 judges to which of the Bucky devices 51 the radiographic image capturing apparatus 1 is currently loaded, which of the radiation sources 52 (see FIG. 1) of the radiation generator 57 has been activated, which of the Bucky devices 51 is to be irradiated with the radiation, etc., and selects the icon I by which the imaging can be performed without changing the current statues of the apparatuses/devices, or by which the imaging can be performed with the minimum change of the statuses, so as to execute the focus display of the icon I.

Since these points are described in details in WO2011/142157, please see the document for more information. The way of moving the focus display of the icon I is not limited to the above example, and can be arbitrary determined.

Although the console 58 is configured so as to automatically move the focus display of the icon I as described above, for example, when the operator such as the radiologist clicks the specific icon I and the same is displayed in the focused manner, it is also possible to perform the focused display of the icon I specified by the operator, not the icon I which the console 58 has automatically selected.

The console 58 thus automatically moves the focus display of the icon I, or performs the focus display of the icon I according to the instruction of the operator as described above, and then transmits the predetermined information including the tube voltage and/or irradiation time (and the tube current, if it needs to be set) to the radiation generator 57 (see FIG. 1), on the basis of the imaging conditions (i.e. the "Imaging Portion" P7, "Imaging Direction" P8, etc.) specified by the imaging order information corresponding to the icon I displayed in the focused manner. Thus, the console 58 of the embodiment automatically executes the setting of the tube voltage and the like to the radiation generator 57, on the basis of the imaging order information corresponding to the icon I to which the focus display has been moved, every time the focus display of the icon I is moved.

Incidentally, when the tube voltage and the like are set in the radiation generator 57, without waiting for the operation by the operation such as the radiologist, the radiation generator 57 makes preparations, by activating the unactivated radiation source 52, changing the tube voltage which needs to be changed, or other means, so that the imaging specified by the imaging order information corresponding to the icon I, to which the focus display has been moved, can be swiftly performed. According to such configuration, since the radiation generator 57 automatically makes preparations for the next imaging, without waiting for the preparation by the operator, when the tube voltage and the like are set by the console 58, the operator can promptly start the next imaging, and thereby the advantage that the next imaging can be swiftly performed is obtained.

In the embodiment, the imaging specified by the imaging order information corresponding to the icon I displayed in the focused manner on the screen H2 of the console 58 is performed as described above, and when the image data DP for preview image is transmitted from the radiographic image capturing apparatus 1, the console 58 generates the preview image P_PRE based on the image data DP for preview image. The console 8 then displays the generated preview image P_PRE in the display working space S in the center of the screen H2.

The console 58 shifts the processing to a generating process of the radiographic image P immediately after displaying the preview image P_PRE. When the operator such as the radiologist does not instruct the console 58 to retake the radiographic image, by not clicking a not-illustrated "Retake" button icon on the screen H2, during a predetermined time period in which the preview image P_PRE is displayed, the console 58 judges that the preview image P_PRE is approved by the operator.

Incidentally, there may also be adopted a configuration where an operator such as a radiologist who has seen the displayed preview image P_PRE can approve the preview image P_PRE, without waiting for a lapse of the predetermined time period, for example, by clicking a not-illustrated "OK" button icon or the like.

When the operator who has seen the displayed preview image P_PRE does not approve the preview image P_PRE and instructs the console 58 to retake the radiographic image, the console 58 instructs the radiographic image capturing apparatus 1 to stop the operation executed at that time, and to start processing for retaking, such as resetting the radiation detecting elements 7. The console 58 also performs processing such as deleting, from the storage member 59 (see FIG. 1), the image data DP for preview image and/or the image data D transmitted from the radiographic image capturing apparatus 1 for the current imaging, because they are not necessary in the next imaging.

The timing of displaying the thumbnail image PT of the preview image P_PRE in the space ST in the vicinity of the icon I may be same as the timing of displaying the preview image P_PRE in the display working space S in the center of the screen H2, or may be a point of time when a predetermined time has passed since the preview image P_PRE is displayed in the display working space S in the center of the screen H2, and thereby the preview image P_PRE is regarded as being approved by the operator.

The console 58 thus generates the preview image P_PRE and displays the thumbnail image PT thereof in the space ST, and subsequently performs the generating processing of the radiographic image P on the basis of the transmitted image data D and the like. When the radiographic image P is generated, the console 58 displays the thumbnail image PT of the generated radiographic image P so as to overwrite the above-described thumbnail image PT of the preview image P_PRE displayed in the space ST.

[Regarding Configuration Specific to the Present Invention]

The console 58 displays the thumbnail images PT of the preview image P_PRE and the radiographic image P in the focused manner, similarly to the above-described focus display of the icon I. Concretely, the thumbnail images PT of the preview image P_PRE and the generated radiographic image P are displayed in the focused manner, in a different way from those of other thumbnail images, by being enclosed with the frame, or other means.

When the currently-executed generating process of the radiographic image P ends, the radiographic image P is displayed so as to overwrite the image in the display working space S in the center of the screen H2, and displays the thumbnail image PT of the radiographic image P to overwrite the thumbnail image PT of the preview image P_PRE displayed in the space ST.

When a not-illustrated enter button is operated with respect to the overwritten radiographic image P displayed in the display working space S, for example, when a not-illustrated "OK" button icon is clicked, the console 58 moves the focus display of the thumbnail image PT to a position of the space ST in which the thumbnail image of the preview image P_PRE or the radiographic image P generated based on the image data D obtained by the next imaging is to be displayed.

In the embodiment, the displayed overwritten radiographic image P is regarded as being confirmed (hereinafter sometimes referred to as "deemed confirmation") by the operator, at the time point when the predetermined time has passed since the overwritten/displayed radiographic image P is displayed in the display working space S, and the focus display of the thumbnail image PT is moved to the position of the space ST in which the thumbnail image of the preview image P_PRE or the radiographic image P generated based on the image data D obtained by the next imaging is to be displayed.

Incidentally, in the embodiment, the radiographic image P is correlated to the imaging order information even when the deemed confirmation of the radiographic image P is thus performed.

The console 58 has two modes of a first transition mode in which the transition of the focus display of the icon I and the transition of the focus display of the thumbnail image PT are performed concurrently, and a second transition mode in which each of the transition of the focus display of the icon I and the transition of the focus display of the thumbnail image PT may be independently performed. The console 58 can switch the transition mode of the focus displays between the first transition mode and the second transition mode.

Hereinafter the way of transition of the focus displays of the icon I and the thumbnail image PT in each of the modes will be specifically described.

When the first transition mode is set as the transition mode of the focus displays, the console 58 controls the way of displaying in the screen H2 so that the transition of the focus display of the icon I and the transition of the focus display of the thumbnail image PT are performed concurrently as described above.

Figure 12:
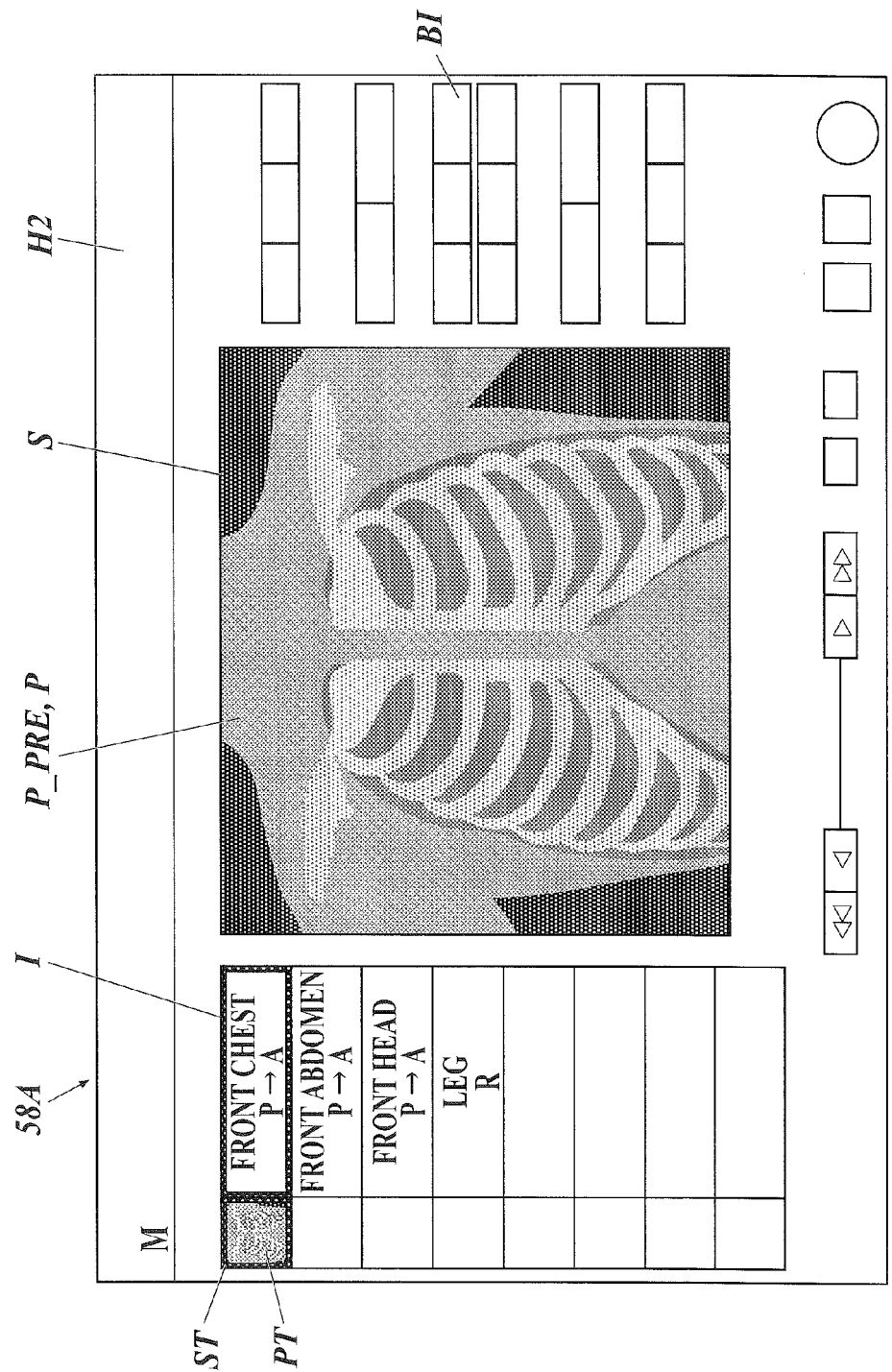
FIG. 12 is a diagram for explaining about a state that a thumbnail image of a preview image is displayed in the vicinity of an icon while the preview screen is displayed in a display working space in the center of a screen.

In this case, for example, even when the "Retake" button icon is not clicked during the predetermined time period in which the preview image P_PRE is displayed in the screen H2 and thereby the preview image P_PRE is approved in the state illustrated in FIG. 12, the focus display of the icon I is not immediately moved to the icon I of the next imaging, and the state illustrated in FIG. 12 is maintained.

When the generating process of the radiographic image P is completed, the console 58 displays the generated radiographic image P so as to overwrite the preview image P_PRE displayed in the display working space S in the center of the screen H2, and displays the thumbnail image PT of the generated radiographic image P so as to overwrite the thumbnail image PT of the preview image P_PRE displayed in the space ST in the vicinity of the icon I.

After that, when the operator such as the radiologist operates the enter button, namely, e.g. clicks the "OK" button icon, with respect to the radiographic image P displayed in the display working space S on the screen H2, after performing the image quality adjustment by operating the button icon BI for the image quality adjustment or other means, or without operating the button icon BI for the image quality adjustment if he/she judges that the image quality adjustment is not necessary, the console 58 immediately confirms the radiographic image P and correlates it to the imaging order information, as described above.

Figure 13:
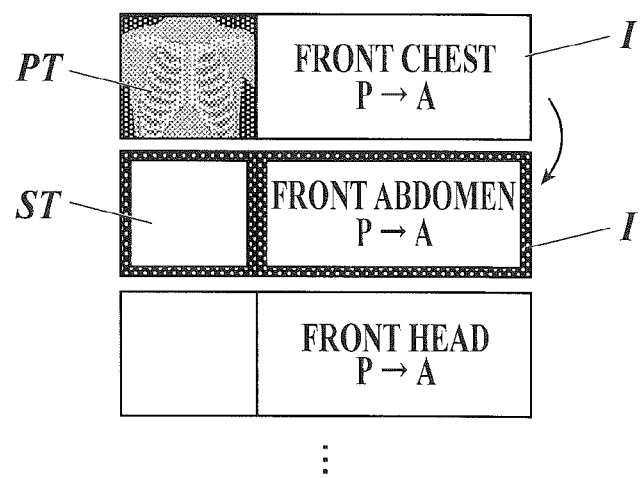
FIG. 13 is a diagram for explaining about a state that a transition of a focus display of an icon and a transition of a focus display of a thumbnail image are simultaneously performed in a first transition mode.

Then, for example, as illustrated in FIG. 13, the console 58 moves the focus display of the icon I to the icon I of the next imaging (i.e. the next imaging in the order of registration of pieces of the imaging order information, or the next imaging when the transition is performed so that the amount of change from the previous imaging state becomes minimum, as described above), and at the same time, moves the focus display of the thumbnail image PT to the position of the space ST in which the thumbnail image PT is displayed in the vicinity of the icon I of the next imaging.

Moreover, as described above, if the operator such as the radiologist does not operate the button icon BI for the image quality adjustment or does not click a not-illustrated "NG" button even when the radiographic image P is displayed in the display working space S on the screen H2, only when the predetermined time has passed since the radiographic image P is displayed, the focus display of the icon I and the focus display of the thumbnail image PT are moved to the position of the icon I of the next imaging and the position of the space ST displaying the thumbnail image PT in the vicinity of the icon I of the next imaging, respectively, as illustrated in FIG. 13.

Incidentally, in the case that the first transition mode is thus set as the transition mode of the focus displays, also when the operator such as the radiologist executes the operation to move the focus display to the specific icon I or space ST in an unimaged-state by clicking the icon I or space ST in the unimaged-state in which the thumbnail image PT is not displayed, the console 58 moves the focus images to the icon I specified by the operator and the position of the space ST displaying the thumbnail image PT in the vicinity of the icon I simultaneously, as described above.

In this case, at the point of time when the transition of the focus display of the icon I and the transition of the focus display of the thumbnail image PT are performed concurrently, the console 58 transmits the predetermined information such as the tube voltage to the radiation generator 57 (see FIG. 1), on the basis of the imaging conditions specified by the imaging order information corresponding to the icon I of the next imaging, so as to execute the setting of the tube voltage and the like to the radiation generator 57.

Meanwhile, in the case that the second transition mode is set as the transition mode of the focus displays, the console 58 controls the way of displaying in the screen H2 so that each of the transition of the focus display of the icon I and the transition of the focus display of the thumbnail image PT is performed independently, as described above.

Figure 14A:
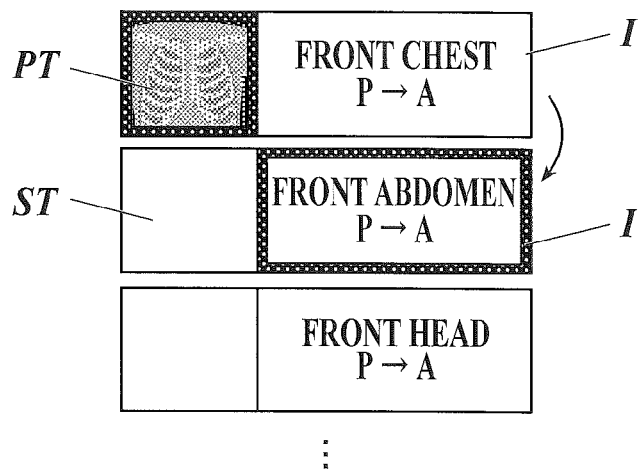
FIG. 14A is a diagram for explaining that the focus display of the icon changes to an icon of next imaging, first, in a second transition mode.

In this case, when the "Retake" button icon is not clicked during the predetermined time period in which the preview image P_PRE is displayed on the screen H2 and thereby the preview image P_PRE is approved in the state illustrated in FIG. 12, the focus display of the icon I is instantly moved to the icon I of the next imaging at that time. However, the transition of the focus display of the thumbnail image PT is not performed because the radiographic image P has not been generated at that time. In this case, as illustrated in FIG. 14A, the focus display of the icon I is firstly moved to the icon I of the next imaging.

Incidentally, the way of moving the focus display of the icon I may be arbitrary determined. As already described, the focus display of the icon I may be moved in the order of registration of pieces of the imaging order information, or may be moved so that the amount of change from the previous imaging state becomes minimum, e.g. may be moved to the icon I of imaging performed by using the same Bucky device.

Figure 14B:
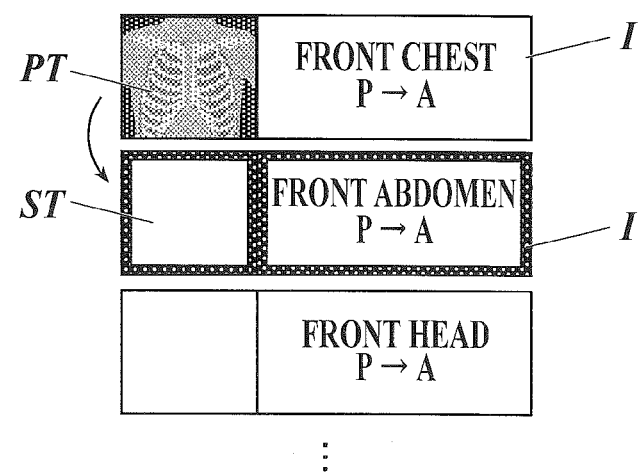
FIG. 14B is a diagram for explaining that the focus display moves to a position of a space, in which the thumbnail image is displayed, in the vicinity of the icon of the next imaging, in the second transition mode, subsequently to FIG. 14A.

The console 8 then completes the generating process of the radiographic image P, displays the radiographic image P so as to overwrite the image in the display working space S in the center of the screen H2, and displays the thumbnail image PT of the radiographic image P so as to overwrite the image in the space S in the vicinity of the icon I. After that, if the operator such as the radiologist does not click the "NG" button till the predetermined time has passed, the console 58 moves the focus display to the position of the space ST, which displays the thumbnail image PT, in the vicinity of the icon I of the next imaging, as illustrated in FIG. 14B.

Incidentally, in this case, at the point of time when the transition of the focus display of the icon I is performed (see FIG. 14A), the console 58 transmits the predetermined information such as the tube voltage to the radiation generator 57 on the basis of the imaging conditions specified by the imaging order information corresponding to the icon I of the next imaging, so as to perform the setting of the tube voltage and the like to the radiation generator 57.

Moreover, in this case, also when the operator such as the radiologist performs the operation to move the focus display to the specific icon I by clicking the icon I, or performs the operation to move the focus display to the specific thumbnail image PT by clicking the thumbnail image PT, the console 58 moves each of the focus displays to the icon I instructed by the operator or to the thumbnail image PT instructed by the operator, independently from each other, as described above.

In this regard, however, in both cases of the first and second transition modes, when the operator clicks the space ST, which is in the unimaged-state and does not display the thumbnail image PT, to move the focus image, the operator is regarded as having an intention to start execution of the imaging order information corresponding to the space ST, which is displayed in the focused manner by the operator, and also the focus display of the icon I is moved to the icon I corresponding to the space ST.

Moreover, in both cases of the first and second transition modes, the operator such as the radiologist executes the above-described image quality adjustment of the radiographic image P on the screen H2 as necessary, and then confirms the radiographic image P, for example, by clicking the not-illustrated "OK" button icon on the screen H2, when it can be judged that the radiographic image P is a proper image as a medical image to be provided for diagnosis.

When the radiographic image P is thus confirmed by the operator, the console 58 correlates the radiographic image P to the imaging order information (i.e. the imaging order information corresponding to the icon I adjacent to the thumbnail image PT of the radiographic image P) based on which the radiographic image P has been captured, and temporarily stores them in the storage member 59 (see FIG. 20).

After that, the console 58 appropriately performs post-imaging processing such as transmitting the radiographic image P correlated to the imaging order information and the like to a predetermined location such as a Picture Archiving and Communication System (PACS) and a Quality Assurance (QA) station, for each imaging, or at a set timing such as a point of time when a series of imaging processes ends.

[Operations]

Next, operations of the radiographic image capturing system 50 and the console 58 (see FIG. 1) of the embodiment having the above configurations will be described. Hereinafter, an example suitable for applying the first transition mode and/or the second transition mode will be described.

Example 1

There is considered as an example a case where an operator such as a radiologist using the radiographic image capturing system 50 and the like is not accustomed to the above-described works, and there is only the second transition mode as the transition mode of the focus display by the console 58, which independently moves each of the focus display of the icon I and the focus display of the thumbnail image PT.

In this case, the focus display of the icon I and the focus display of the thumbnail image PT are moved separately while the operator goes back and forth between the imaging room RA where imaging is performed and the front room RB (see FIG. 1). For this reason, as described above, there is a possibility that the operator who is not accustomed to the works becomes unable to understand which of the images has not been subjected to the image quality adjustment. There is also a possibility that the operator replaces the images with one another by manual operation, and wrongly correlates the image to the imaging order information.

In such a case, if the radiographic image capturing system 50 and/or the console 58 have the configurations of the embodiment, by setting the first transition mode as the transition mode of the focus display of the console 58, it becomes possible to perform setting so that the transition of the focus display of the icon I and the transition of the focus display of the thumbnail image PT are executed concurrently, as illustrated in FIG. 13.

By this setting, the focus displays of the icon I and/or thumbnail image PT are not immediately moved even when the preview image P_PRE displayed on the screen H2 of the console 58 is approved, and the state in which the icon I of the imaging which has been executed until then is displayed in the focused manner is maintained. By this, even the operator not accustomed to the works can recognize which of the icons I corresponds to the radiographic image P currently subjected to the generating process by the console 58, and when the radiographic image P is displayed in the display working space S in the center of the screen H2, the operator can understand that the displayed radiographic image P is the radiographic image P taken by the radiographic imaging executed based on the imaging order information corresponding to the icon I under the focus display.

Thus, the operator can accurately confirm the radiographic image P while looking at the radiographic image P displayed on the screen H2 of the console, after performing the image quality adjusting process of the radiographic image P as necessary. By this, even the operator not accustomed to the works can accurately correlate the confirmed radiographic image P to the imaging order information corresponding to the icon I displayed in the focused manner.

As described above, according to the radiographic image capturing system 50 and/or the console 58 of [Example 1], even the operator not accustomed to the works can accurately adjust the image quality of the radiographic image P and surely correlate the radiographic image P to the imaging order information, by setting the first transition mode as the transition mode of the focus display. Furthermore, the operator not accustomed to the works can perform the above works at ease, and the problems that the operator wrongly correlates the radiographic image P and the imaging order information to each other, and/or forgets to perform the image quality adjustment can be properly prevented. Accordingly, the radiographic image capturing system 50 and/or the console 58 becomes convenience for such operator.

Example 2

On the other hand, in the case that an operator such as a radiologist using the radiographic image capturing system 50 and the like is accustomed to the above-described works, the operator confirms only necessity of retake by looking at the preview image P_PRE displayed on the screen H2 of the console 58, and performs a series of imaging processes first, while postponing the confirming process of the radiographic image P. The operator often wants to perform these confirming processes simultaneously later. Such processing is more convenient also for a patient, because a waiting time of the patient as an object is reduced and thereby the imaging will end early.

In such as case, if the radiographic image capturing system 50 and the console 58 are configured as described in the embodiment, by selecting and setting the second transition mode (see FIGS. 14A and 14B) as the transition mode of the focus displays of the console 58, it becomes possible to perform the setting of the tube voltage and the like to the radiation generator 57 for the next imaging more quickly, and thereby the operator can execute one imaging after another.

Concretely, when the first transition mode is set as the transition mode of the focus display as described above (see [Example 1], for example), the console 58 firstly displays the preview image P_PRE. The console 58 does not move the focus display of the icon I to the icon I of the next imaging until the predetermined time has passed since then, and until the predetermined time has passed since the radiographic image P has been generated and displayed. By this, the timing to transmit the information such as the tube voltage for the next imaging becomes a timing after the predetermined time has passed since the radiographic image P has been displayed.

Meanwhile, when the second transition mode is set as the transition mode of the focus display as in the case of [Example 2], the console 58 moves the focus display of the icon I to the icon I of the next imaging at a point of time when the predetermined time has passed since the preview image P_PRE has been displayed (without waiting generation and display of the radiographic image P).

For this reason, the timing to transmit the information such as the tube voltage for the next imaging becomes earlier than that in the case of the first transition mode. At a point of time when the operator who has looked and confirmed the preview image P_PRE moves to the imaging room RA, the setting of the tube voltage and the like to the radiation generator 57 is already completed, and the radiation generator 57 swiftly becomes ready for the next imaging. Accordingly, the operator can successively capture the radiographic images.

Incidentally, in this case, the console 58 automatically moves the focus display of the thumbnail image PT to the thumbnail image PT (more accurately, the space ST in which the thumbnail image PT is displayed) corresponding to the icon I of the next imaging, at a point of time when the predetermined time has passed since the generated radiographic image P has been displayed. By this, as illustrated in FIG. 14A and FIG. 14B, the focus display of the thumbnail image PT moves so as to follow the transition of the focus display of the icon I on the screen H2.

Moreover, the focus displays of the icon I and/or the thumbnail image PT can be manually moved by the operator, for example, by clicking the icon I or the thumbnail image PT, as described above. Thus, after the series of imaging processes is completed, the operator can move the focus display of the thumbnail image PT by the operation such as clicking the thumbnail image PT, and perform the confirming process of the radiographic image P, which has not been subjected to the confirming process corresponding to the thumbnail image PT, namely, which has been unconfirmed.

Thus, by moving the focus display of the thumbnail image PT to the intended thumbnail image PT of the radiographic image P by clicking the thumbnail image PT or another way, the generated but unconfirmed radiographic image P is displayed in the display working space S in the center of the screen H2. Moreover, by executing the confirming process of the radiographic image P after executing the image quality adjusting process as necessary, the radiographic image P is confirmed and accurately correlated to the corresponding imaging order information.

Thus, according to the radiographic image capturing system 50 and/or the console 58 of [Example 2], the operator accustomed to the works can accurately perform the image quality adjustment to the radiographic image P, and reliably correlate the radiographic image P to the imaging order information. Moreover, by setting the second transition mode as the transition mode of the focus display, the operator accustomed to the works can successively image the radiographic images. Accordingly, imaging efficiency can be further improved and the radiographic image capturing system 50 and/or the console 58 become easier to be used by such operator.

As described in [Example 1] and [Example 2], the console 58 can be configured to set the transition mode of the focus displays to the first transition mode or the second transition mode, depending on the operator who performs processing by using the console 58, namely, depending on whether or not the operator is accustomed to the works (i.e. depending on workmanship/skill of the operator).

In such a case, for example, it is possible to previously prepare a table in which each piece of identification information such as a name and/or ID of the operator is correlated to any of the transition modes, so that when the identification information of the operator is input prior to the imaging, the console 58 refers to the table to automatically set the transition mode correlated to the operator on the basis of the input identification information.

By thus setting the transition mode of the focus displays in the console 58 depending on the operator, the operator who is not accustomed to the works can move the focus displays of the icon I and/or the thumbnail image PT in the first transition mode, and the operator who is accustomed to the works can move the focus displays of the icon I and/or the thumbnail image PT in the second transition mode, and thereby the effects described in [Example 1] and [Example 2] can be effectively produced, respectively.

Incidentally, preferably, the correlation between each piece of the identification information of the operator and each of the transition modes can be appropriately updated, for example, depending on the number of times of the imaging using the radiographic image capturing system 50 and/or the console 58, depending on the fact that the operator has passed a technical skills test, and/or depending on whether or not the operator has voluntarily made a declaration. It is also preferable that the transition mode can be switched as needed, when the operator has voluntarily made the declaration. According to such configuration, the transition mode can be arbitrary changed depending on workmanship/preference of the operator, and thereby efficiency/certainty of the works can be improved.

There is expected a case where the transition mode of the focus displays is switched between the first transition mode and the second transition mode after the imaging is started, depending on the status of the imaging order information. For example, when the imaging order information instructing to capture a plurality of images of one (1) patient is mixed in the middle of a series of pieces of imaging order information each instructing to image one (1) image of one (1) patient, there is expected a use mode where the transition mode is changed to the second transition mode to prioritize the imaging of the plurality of images in order to release the patient from a restraining state for the imaging in an early stage, and the transition mode is then returned to the first transition mode when the imaging of the plurality of images ends in order to prevent mistakes from occurring in the correlation. In such a case, for example, it is preferable to make the transition mode capable of being switched when a photographer such as a radiologist operates a not-illustrated transition mode changing button.

In the above case, the following configuration may be adopted. Concretely, when the console 58 judges that there are no another pieces of the imaging order information including the patient information same as the patient information contained in the selected imaging order information, and having not subjected to the imaging, the transition mode is automatically set to the first transition mode. When the next imaging order information is specified after the imaging, and when there is the imaging order information including the patient information same as the patient information contained in the selected imaging order information, and having not subjected to the imaging, the transition mode may be automatically set to the second transition mode.

Example 3

With respect to the radiographic image capturing system 50 illustrated in FIG. 1, the case where one (1) person as the operator such as the radiologist goes back and forth between the imaging room RA and the front room RB to perform the imaging, the image quality adjusting process and/or the confirming process, is described. However, for example, there may also be a case where the works are shared so that one operator (e.g. a radiologist having little experience) performs the imaging and another operator (e.g. an upper class radiologist) performs the image quality adjusting process and the confirming process.

In the case that the operator who executes the imaging in the imaging room RA is different from the operator who executes the confirming process of the radiographic image P and the like by using the console 58 as described above, the operator executing the imaging is expected to wish to successively image the radiographic images while entrusting the different operator to execute the confirming process of the radiographic image P and the like. The operator executing the confirming process of the radiographic image P and the like is expected to wish to perform the image quality adjusting process and the confirming process of the radiographic image P independently from the imaging executed by the different operator.

For this reason, in the case that the operator who executes the imaging in the imaging room RA is different from the operator who executes the confirming process of the radiographic image P and the like by using the console 58, it is preferable to set at least the transition mode of the focus display on the screen H2 of the console 58 to the second transition mode. Concretely, it is preferable to perform setting such that each of the transition of the focus display of the icon I and the transition of the focus display of the thumbnail image PT of the preview image P_PRE or the radiographic image P, the thumbnail image PT being displayed in the vicinity of the icon I, is performed independently.

Thus, according to the radiographic image capturing system 50 and/or the console 58 of [Example 3], by setting the second transition mode as the transition mode of the focus displays, each of the transition of the focus display of the icon I and the transition of focus display of the thumbnail image PT can be performed independently. By this, the operator who executes the imaging in the imaging room RA can move the focus display of the icon I, while the operator who executes the confirming process of the radiographic image P, etc., on the console 58 can move the focus display of the thumbnail image PT. Thus, each of the operators can freely perform his/her task without being bound by the works of other operators.

The operator who executes the confirming process of the radiographic image P, etc. can accurately perform the image quality adjustment to the radiographic image P and can confirm the radiographic image P so that the confirmed radiographic image P is certainly correlated to the imaging order information, and at the same time, the operator who executes the imaging can successively capture the radiographic images P because he/she does not need perform the confirming processes of the radiographic images P. Accordingly, imaging efficiency can be further improved.

Moreover, as described in [Example 3], the console 58 may be configured to set the transition mode of the focus displays to either the first transition mode or the second transition mode, depending on whether the operator who executes the imaging in the imaging room RA is the same or different person as/from the operator who executes the confirming process of the radiographic image P, etc., on the console 58.

Incidentally, in the configuration of [Example 3], if the radiographic image capturing system 50 is configured such that the operator such as the radiologist, who executes the imaging, bothers to move to the location of the console 58 in the front room RB in order to perform the transition of the focus display of the icon I, and/or requests another operator, who executes the confirming process of the radiographic image P, etc., on the console 58, to perform the transition of the focus display of the icon I, there is a possibility that working efficiency is lowered.

Figure 15:
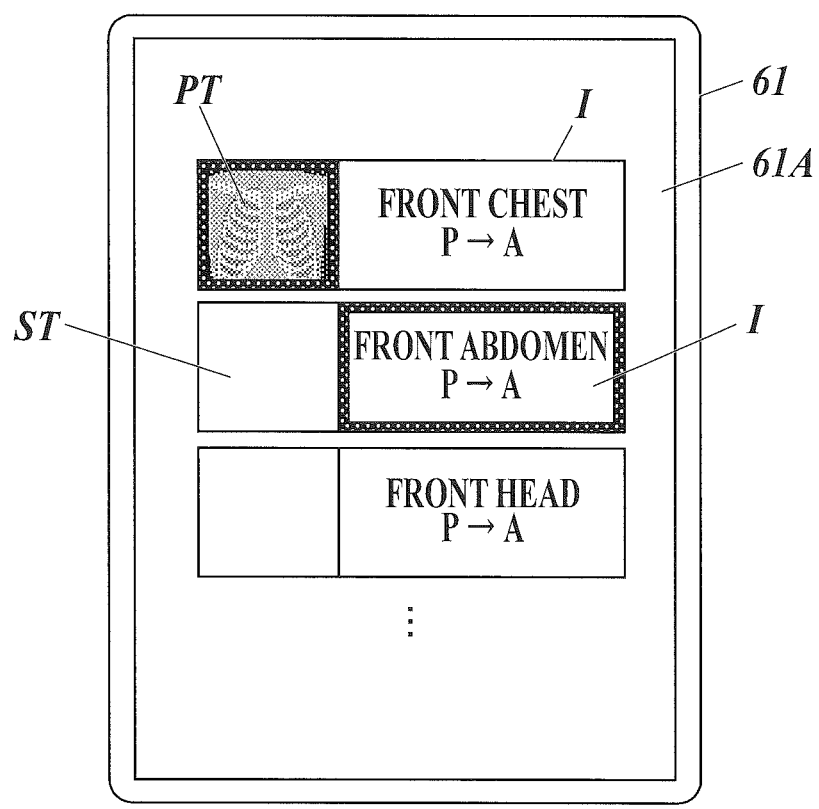
FIG. 15 is a diagram illustrating a configuration example of a portable terminal, in which icons are displayed on a screen of the portable terminal, the icons being same as icons displayed on the console.

For this reason, in the configuration of [Example 3], it is preferable to configure the radiographic image capturing system 50 so as to make the operator executing the imaging carry, for example, a portable terminal 61 illustrated in FIG. 15, and to make the portable terminal 61 display the icon I, which is same as the icon I displayed in the console 58, in a screen 61A of the portable terminal 61.

The operator executing the imaging needs to look at the preview image P_PRE in order to judge whether or not the retake is necessary. For this reason, the portable terminal 61 may be configured, for example, such that the thumbnail image PT of the preview image P_PRE is displayed in the vicinity of the icon I, as illustrated in FIG. 15, similarly to the case of the console 58. In such a case, it is possible to display the thumbnail image PT of the preview image P_PRE so that it becomes larger than the thumbnail image PT displayed on the console 58 in order to make the thumbnail image PT of the preview image P_PRE easier to be looked, or to display the enlarged preview image P_PRE on the screen 61A, for the above-described predetermined time.

Incidentally, the radiographic image capturing system 50 may be configured such that when the operator looking at the preview image P_PRE judges that the retake is necessary, the portable terminal 61 transmits a signal(s) to the radiographic image capturing apparatus 1 though the console 58, or directly, to instruct the radiographic image capturing apparatus 1 to start preparation for the retake. Also the radiographic image capturing apparatus 1 may be configured to transmit the image data DP for preview image to the portable terminal 61 directly, or through the console 58.

Furthermore, in the configuration of [Example 3], if the radiographic image capturing system 50 is configured so that the operator, who executes the confirming process of the radiographic image P, etc., on the console 58, can move the focus display of the icon I, there is a possibility that the focus display of the icon I is moved despite the intention of the operator who executes the imaging, and this may cause confusion during the imaging. In this case, there may be a situation that the generated radiographic image P is wrongly correlated to uncorresponding imaging order information.

For this reason, in the configuration of [Example 3], it is preferable to prohibit the operator from moving the focus display of the icon I in the console 58 used by the operator who executes the confirming process of the radiographic image P, etc., on the console 58, and to allow the operator to move the focus display of the icon I only in the portable terminal 61 carried by the operator who executes the imaging. During that time period, only the confirming process of the radiographic image P and the like are allowed in the console 58.

Although the focus display of the icon I cannot be moved in the console 58 in this case, it is also possible to configure the radiographic image capturing system 50 such that also the focus display of the icon I moves on the screen H2 of the console 58 so as to follow the transition/movement of the focus display of the icon I on the screen 61A of the portable terminal 61 performed by the operator who executes the imaging. In this case, it is also possible to configure the console 58 such that the focus display of the icon I is not performed, namely, such that only the icons I not to be displayed in the focused manner are displayed.

Such configuration can accurately prevent the operator, who executes the confirming process of the radiographic image P and the like, from moving the focus display of the icon I, despite the intention of the operator who executes the imaging, and the operator who executes the imaging can accurately perform the imaging without confusion. The configuration can also prevent the generated radiographic image P from being wrongly correlated to the uncorresponding imaging order information, and thereby the radiographic image P can be certainly correlated to the imaging order information.

In such a case, contrary to the above, it is preferable to configure the portable terminal 61 such that the operator is prohibited from moving the focus display of the thumbnail image PT. Additionally, the operator who executes the imaging would sometimes wish to check the preview image P_PRE (or the radiographic image P), which has been previously captured, again. In such a case, the portable terminal 61 may be configured such that the operator can perform the transition of the focus display of the thumbnail image PT on the screen 61A of the portable terminal 61, independently from or with no relation to the transition of the focus display of the thumbnail image PT in the console 58.

Example 4

Figure 16:
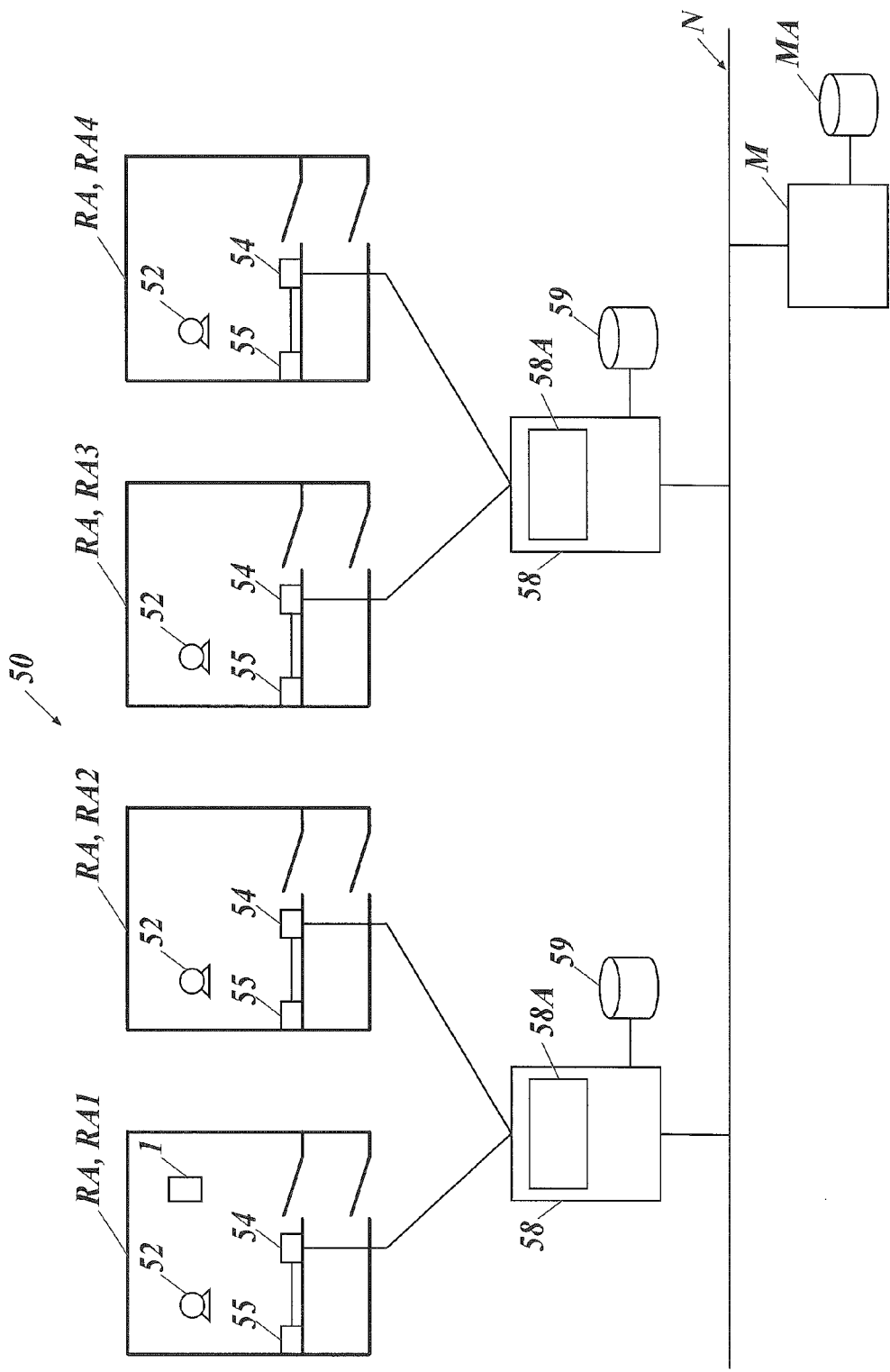
FIG. 16 is a diagram for explaining about a configuration example of the radiographic image capturing system in which a plurality of imaging rooms are correlated to one (1) console.

The configuration of [Example 3] can also be applied, for example, to the radiographic image capturing system 50 in which a plurality of imaging rooms RA are correlated to one (1) console 58, as illustrated in FIG. 16.

In this case, the operators who execute the imaging exist in the imaging room RA1 and the imaging room RA2 illustrated in FIG. 16, respectively, and each of the operators successively captures the radiographic images. The consoles 58 may perform the generating processes of the radiographic images P which have been taken in the imaging room RA1 and the imaging room RA2, the consoles 58 being correlated to the imaging room RA1 and the imaging room RA2, respectively, and disposed outside the imaging rooms. The operators allocated to the consoles 58, respectively, can successively execute the image quality adjusting processes and/or the confirming processes of these radiographic images P.

Also in this case, the transition mode of the focus displays in the console 58 and/or the portable terminals 61 carried by the operators in the imaging rooms RA1, RA2 is set to the second mode, namely, the transition mode in which the transition of the focus display of the icon I is executed independently from the transition of the focus display of the thumbnail image PT.

According to the radiographic image capturing system 50 and/or the console 58 of [Example 4], by setting the second transition mode as the transition mode of the focus displays, the focus display of the icon I and the focus display of the thumbnail image PT can move independently from each other. Accordingly, each of the operators who execute the imaging in the imaging rooms RA1, RA2 can freely move the focus display of the icon I, and each of the operators who execute the confirming process of the radiographic image P and the like on the console 58 can freely move the focus display of the thumbnail image P, and thereby each of them can perform his/her task without being bound by the works of other operators.

Thus, the operator who executes the confirming process of the radiographic image P and the like can accurately execute the image quality adjustment to the radiographic image P, can confirm the radiographic image P, and can certainly correlate the confirmed radiographic image P to the imaging order information, and the operator who executes the imaging can successively image the radiographic images P at his/her own pace because he/she does not need to perform the confirming process of the radiographic image P, and thereby imaging efficiency can be further improved.

Incidentally, in this case, the operators in the imaging rooms RA may share roles to perform the imaging, for example, by executing in the imaging room RA1 only the imaging using the Bucky device 51Y for standing position imaging, and executing in the imaging room RA2 only the imaging using the Bucky device 51X for lying position imaging, or executing in the imaging room RA2 only the imaging using the radiographic image capturing apparatus 1 which is not loaded into the Bucky device 51 and is used independently.

At that time, the console 58 may determine, on the basis of the "Bucky ID" P9 (see FIG. 10, etc.) described in the series of pieces of the imaging order information obtained from the RIS and the like, which of the imaging rooms includes the Bucky device 51 having the Bucky ID, namely, which of the imaging rooms is used for the imaging related to the imaging order information, and may allocate the imaging order information to the determined imaging room to transmit the imaging order information thereto.

Each of the imaging rooms RA1, RA2 may be used for each patient. In this case, the console 58 may discriminate pieces of the imaging order information from one another for each patient, and simultaneously transmit a piece of or pieces of the imaging order information for each patient, to each of the imaging rooms. Alternatively, the console 58 may transmit the common imaging order information to the imaging rooms RA1, RA2, and the portable terminal 61 in each of the imaging rooms RA may discriminate necessary imaging order information from the others. In this case, it is needless to say that mutual exclusion is performed so that the imaging order information selected by one (1) portable terminal 61 cannot be selected by other portable terminals 61.

Example 5

In the case that an operator using the radiographic image capturing system 50, such as a radiologist, is accustomed to the works, for example, when the imaging room RA and the console 58 are correlated to each other on a one-to-one basis as illustrated in FIG. 1, and when one (1) operator executes the confirming process of the radiographic image P and the like while monopolizing the imaging room RA and the console 58, by setting the transition mode of the focus displays to the second transition mode in the console 58 as described in [Example 2], the operator accustomed to the works can certainly correlate the radiographic image P to the imaging order information while successively capturing the radiographic images P.

However, for example, in the case that a plurality of operators accustomed to the works (the same can be said for the case of operators unaccustomed to the works) perform the imaging in the imaging rooms RA3, RA4, in the radiographic image capturing system 50 where the plural imaging rooms RA3, RA4 are correlated to one (1) console 58, it is sometimes better not to apply the configuration of [Example 2].

Hereinafter described is a case where an operator A uses the imaging room RA3 to perform the imaging, an operator B uses the imaging room RA4 to perform the imaging, and the operator A and the operator B share one (1) console 58 correlated to each of the imaging rooms RA3, RA4 to perform the confirming processes of the radiographic images P, respectively.

When applying the configuration of [Example 2] to such case, the transition mode of the focus displays in the console 58 is set to the second transition mode, namely, the mode in which the transition of the focus display of the icon I is performed independently from the transition of the focus display of the thumbnail image PT, and the operator can move each of the focus display of the icon I and the focus display of the thumbnail image PT independently from each other.

However, for example, if each of the operator A and the operator B freely moves the focus display of the icon I and/or the focus display of the thumbnail image PT on the console 58, the operators would be confused about the statuses of the focus displays. Each of the operators could not understand which of imaging tasks has been completed among imaging tasks handled by the operator himself/herself, even when looking at the focus display of the icon I, and could not recognize which of radiographic images P has been subjected to the confirming process and the like, even when looking at the focus display of the thumbnail image PT.

For this reason, a state of confusion may be occur, such that the operator confirms the radiographic image, which is not handled by the operator himself/herself, and correlates the confirmed radiographic image P to the imaging order information, without asking, and/or such that the operator forgets to perform the confirming process of the radiographic image P and/or correlation to the imaging order information.

For this reason, when the plural operators share one (1) console 58, namely, when each of the operators performs both of the imaging and the confirming process of the radiographic image P, without sharing the roles such as the imaging and the confirming process of the radiographic image P, it is preferable to adopt the configuration to set the transition mode of the focus displays in the console 58 to the first transition mode, namely, the transition mode in which the transition of the focus display of the icon I and the transition of the focus display of the thumbnail image PT are performed concurrently.

In this case, for example, the operator, who has executed the imaging in the imaging room RA, moves to the location of the console 58, and instantly performs the confirming process of the radiographic image P and the like to correlate the radiographic image P to the imaging order information, then and there. Then, the operator, who perform the imaging next, concurrently performs the transition of the focus display of the icon I and the transition of the focus display of the thumbnail image PT to declare that the operator himself/herself will execute the next imaging, and immediately after the imaging has been performed, executes the confirming process of the radiographic image P and the like to correlate the radiographic image P to the imaging order information. Such works are repeatedly performed.

Thus, according to the radiographic image capturing system 50 and/or the console 58 of [Example 5], by setting the first transition mode as the transition mode of the focus displays, the state of confusion where the operator makes the radiographic image P, which is not in his/her charge, confirmed, without asking, and correlates it to the imaging order information, and/or confusion where the operator forgets to correlate the radiographic image P to the imaging order information, can be prevented from occurring. Accordingly, the confirming process of the radiographic image P and the like are accurately performed and the radiographic image P is certainly correlated to the imaging order information.

Moreover, as described in [Example 4] and [Example 5], the console 58 may be configured to set the transition mode of the focus displays to the first transition mode or the second transition mode, depending on the use mode of the console 58, for example, depending on whether it is in the use mode in which the operators share the roles to perform the imaging and the confirming process of the radiographic image P and the like, or in the use mode in which each of the operators performs the imaging and the confirming process of the radiographic image P and the like independently.

Example 6

The examples of [Example 1] to [Example 5] illustrate the case where the console 58 sets the transition mode of the focus displays to the first transition mode or the second transition mode, depending on the operator who executes the processing by using the console 58 (in the case of [Example 1] or [Example 2]), depending on whether the operator who executes the imaging in the imaging room RA is the same person as the operator who executes the confirming processing of the radiographic image P and the like on the console 58 or a different person (in the case of [Example 3] or [Example 4]), or depending on the use mode of the console 58 (in the case of [Example 5]).

However, for example, the radiographic image capturing system 50 may be configured, as illustrated in FIG. 16, to include a management apparatus M connected to the single console 58 or the plurality of consoles 58 via a network N or the like, the management apparatus M setting the transition mode of the focus displays to the first transition mode or the second transition mode depending on the operator who executes the processing by using the console 58, depending on whether the operator executing the imaging in the imaging room RA is the same person as the operator executing the confirming processing of the radiographic image P and the like on the console 58 or a different person, or depending on the use mode of the console 58.

According to this configuration, the console 58 can inquire to the management apparatus M about which of the first transition mode and the second transition mode the transition mode of the focus displays should be set to, instead of judging about that by itself to set the transition mode of the focus displays to the first transition mode or the second transition mode, and thereby a processing load in the console 58 can be reduced.

Moreover, by providing the management apparatus M in the radiographic image capturing system 50 equipped with the plurality of consoles 58 as illustrated in FIG. 16, even when the operator using the system and/or the use mode of the console 58 change and thereby it becomes necessary to change the program for setting the transition mode of the focus displays to the first transition mode or the second transition mode, the management apparatus M just have to change only programs stored in the storage member MA thereof, and operations such as installing the changed programs on the consoles 58 are not necessary. Accordingly, there can be obtained effects that the programs are easily and accurately changed.

[Effects]

As described above, the radiographic image capturing system 50 and/or the console 58 are configured to have, as the transition mode of the focus display in the console 58, the first transition mode in which the transition of the focus display of the icon I and the transition of the focus display of the thumbnail image PT of the radiographic image P or the like are performed concurrently, and the second transition mode in which each of the transition of the focus display of the icon I and the transition of the focus display of the thumbnail image PT is performed independently, and are also configured such that the transition mode of the focus displays can be switched between the first transition mode and the second transition mode.

By this, even when the operator using the system, such as the radiologist, and/or the use mode change as described above, the radiographic image P can be reliably correlated to the imaging order information, for example, by accurately executing the image quality adjustment to the radiographic image P. Accordingly, it becomes possible to prevent the operator from forgetting to correlate the radiographic image P to the imaging order information, and/or from mistakenly regarding the radiographic image P captured by any of other operators as the radiographic image P captured by the operator himself/herself and performing the confirming process thereof.

[Variation 1]

To prioritize the correlation of the radiographic image P to the imaging order, in a default state, it is preferable to set, as the transition mode of the focus display in the console 58, the first transition mode, namely, the transition mode in which the transition of the focus display of the icon I and the transition of the focus display of the thumbnail image PT of the radiographic image P of the like are performed simultaneously.

Moreover, the configuration where the transition mode of the focus display in the console 58 can be switched depending on the judgment by the operator or the like is preferable.

[Variation 2]

When setting the second transition mode as the transition mode of the focus displays as described above, there is a possibility that the operator forgets to correlate the radiographic image P to the imaging order information.

For this reason, with respect to the radiographic image P for which the confirming process has not been completed, a mark or the like indicating that the confirming process and the like have not been performed to the radiographic image P specified by the thumbnail image PT may be displayed, for example, on or in the vicinity of the thumbnail image PT on the screen H2 (see FIG. 12, etc.) of the console 58. In this case, the mark or the like may be composed of characters such as "unconfirmed", or may be displayed as a specific shape and/or color by which the operator can recognized that the radiographic image P is unconfirmed.

It is also possible to perform a display on the display section 58A of the console 58, by which the operator can easily and clearly recognize which of the radiographic images P (or the thumbnail images PT) is unconfirmed, instead of displaying the mark or the like on or in the vicinity of the thumbnail image PT. Moreover, for example, when there is the radiographic image P to which the confirming process and the like have not been performed at a point of time when the operator mostly finishes the series of the processes, it is possible to warn the operator of that fact by a display, sound, and the like.

[Variation 3]

In the case that there is many radiographic images to be captured, the icons I and the like sometimes cannot be included within one (1) screen, and extend over next page and/or a subsequent page(s), when the icon I and/or the thumbnail image PT (including the case where no thumbnail image PT is displayed and only the space(s) ST is displayed) are displayed on the screen H2 as illustrated in FIG. 11 and FIG. 12.

In such a case, if the second transition mode in which the transition of the focus display of the icon I can be executed independently from the transition of the focus display of the thumbnail image PT, and vice versa, is set as the transition mode of the focus displays, there may be a case where the focus display of the icon I is performed in a page different from that in which the focus display of the thumbnail image PT is performed.

In this case, if the operator can understand, on the screen H2, which of pages the focus display of the icon I and/or the focus display of the thumbnail image PT are performed in, namely, the whereabouts of the focus displays, the operator such as the radiologist could easily perform the works. For this reason, a configuration to display the whereabouts of the focus displays on the screen H2 is preferable.

Figure 17:
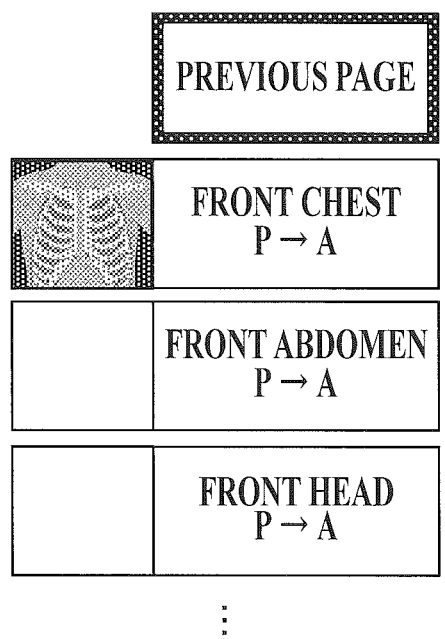
FIG. 17 is a diagram illustrating a display example on a screen representing that the focus display of the icon is performed in a previous page of a currently-opened page.

For example, when the focus display of the icon I is performed in a previous/last page of a current page or in a further previous page(s), it is possible to display, as if the focus display is performed, characters such as "PREVIOUS PAGE" and "PAGE BEFORE LAST" while enclosing the characters with a frame, as in the case of the focus display of the icon I, above the uppermost displayed icon I as illustrated in FIG. 17.

Incidentally, though the characters of "PREVIOUS PAGE" are enclosed with the black-colored frame in FIG. 17, as in the case of the focus display of the icon I or the like, actually, by enclosing the characters with a bright color frame on the screen H2 of a black or dark gray, the operator such as the radiologist can easily and accurately recognize the display.

Moreover, though illustration is omitted, when the focus display of the thumbnail image PT is performed in the previous page of the currently-opened page or the further previous page, similarly to the above, it is possible to display the characters such as "PREVIOUS PAGE" and "PAGE BEFORE LAST" while enclosing the characters with the frame, above the uppermost displayed icon I. Meanwhile, when the focus display of the icon I or the thumbnail image PT is performed in the next page of the currently-opened page or the subsequent page(s) thereof, it is possible to display the characters such as "NEXT PAGE" and "PAGE AFTER NEXT" while enclosing the characters with the frame, below the lowermost displayed icon I and/or the thumbnail image PT.

By such display, even if the currently-opened page does not include the focus display, the operator can easily and accurately recognize the location of the focus display of the icon I or the thumbnail image PT, and can turn over the page(s) to easily and accurately display the icon I and/or the thumbnail image PT, which are being displayed in the focused manner, on the screen H2.

Moreover, it is possible to display a button icon(s), at any position on the screen H2, for automatically skipping to the page in which the icon I and/or the thumbnail image PT are displayed in the focused manner, so that the operator can click the button icon to automatically skip to the page in which the icon I and/or the thumbnail image PT are displayed in the focused manner.

Furthermore, for example, when executing the image quality adjustment and/or the confirming process of the radiographic image P obtained by the currently-executed imaging, namely, the latest radiographic image P, if the focus display of the thumbnail image PT can be moved to the position of the thumbnail image PT of the latest radiographic image P, or to the position of the space ST in which the thumbnail image PT of the latest radiographic image P is to be displayed when the latest radiographic image P has not been generated, the works would become easy.

For this reason, for example, it is also possible to provide a button icon including characters such as "Move to Latest Radiographic Image" at any position on the screen H2, so that the operator can click the button icon so as to move the focus display to the position of the thumbnail image PT of the latest radiographic image P and/or to the position of the space ST in which the thumbnail image PT is to be displayed.

[Variation 4]

There may be a case where the page including no icon I displayed in the focused manner is opened, and it is troublesome to bother to turn over the page(s) so that the icon I displayed in the focused manner is displayed in order to confirm the contents (i.e. the "Imaging Portion" P7 or "Imaging Direction" P8 displayed on the icon I (see FIG. 10, etc.)) of the icon I displayed in the focused manner.

To avoid such troublesome operation, for example, the configuration where the content of the icon I, which is currently displayed in the focused manner, is displayed at any position on the screen H2 may be adopted. This does not disappear and is always displayed even when the page(s) is turned over. The displayed content changes to the content of the icon I, to which the focus display has moved, every time the focus display of the icon I moves.

[Variation 5]

In the meantime, for example, in the case that the operator executing the imaging in the imaging room RA is a different person from the operator executing the confirming process of the radiographic image P and the like on the console 58 as described in [Example 3], the operator, who executes the confirming process of the radiographic image P and the like on the console 58, sometimes cannot understand at which timing the imaging is performed, and at which timing the image data D and/or the image data DP for preview image are transmitted to the console 58 from the radiographic image capturing apparatus 1.

Figure 18:
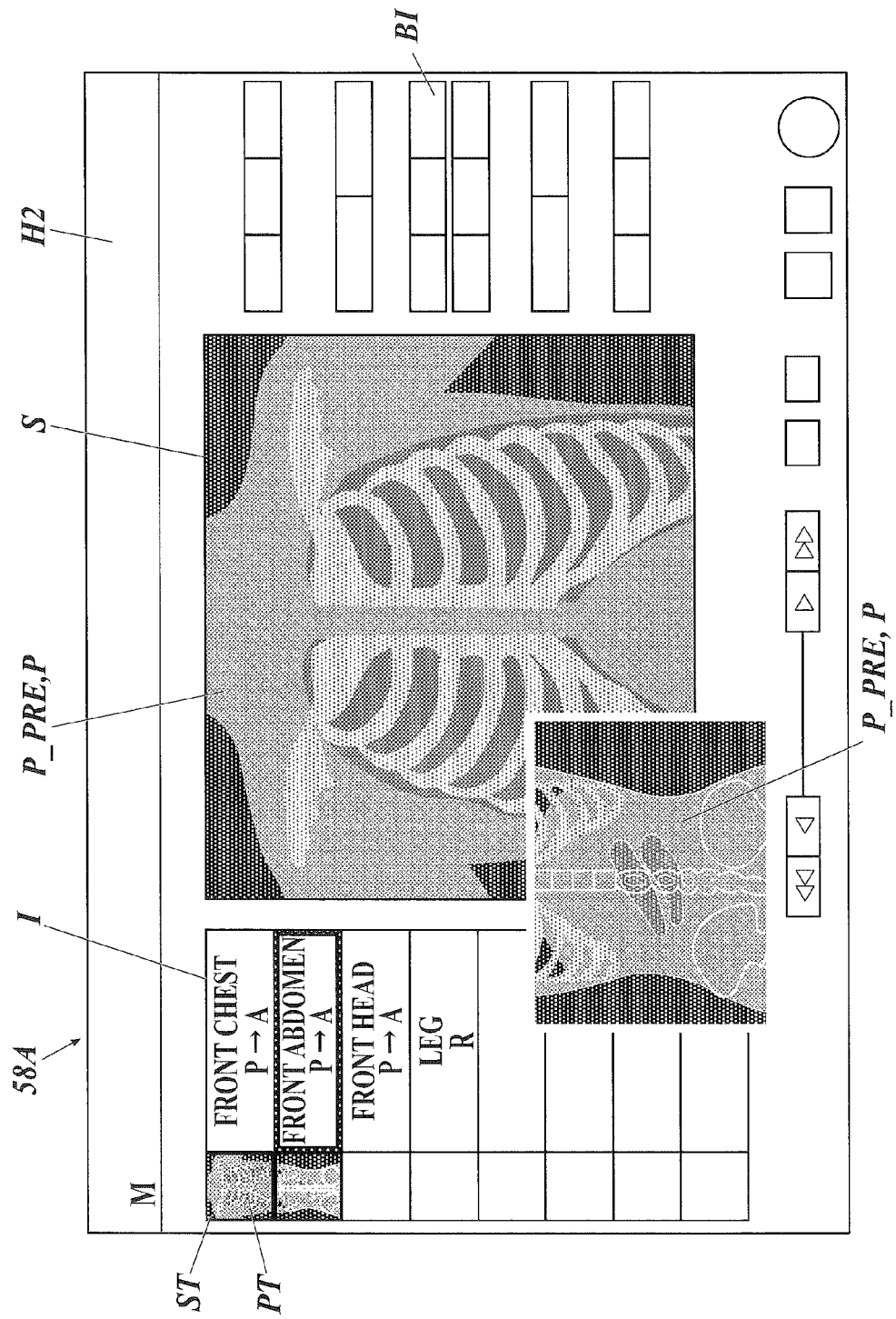
FIG. 18 is a diagram illustrating an example of a case of displaying the preview image and/or the radiographic image in a part of a screen at a point of time when the console generates the preview image and/or the radiographic image.

For this reason, as illustrated in FIG. 18, it is possible to display the generated preview image P_PRE and/or radiographic image P at a part of the screen H2, at a point of time when the imaging has been performed and the console 58 has generated the preview image P_PRE and/or radiographic image P on the basis of the image data DP for preview image, the image data D, etc. transmitted from the radiographic image capturing apparatus 1.

According to this configuration, the operator can easily and surely recognize that the imaging has been performed and the confirming process and the like of the radiographic image P has come to be executable (or will become executable soon) by looking at the preview image P_PRE and/or the radiographic image P displayed in the part of the screen H2.

Incidentally, when the preview image P_PRE and/or the radiographic image P are thus displayed for the new imaging in the part of the screen H2, this sometimes disturbs the currently-executed works such as the confirming process of the radiographic image P. For this reason, there may be adopted a configuration where in the default state, the preview image P_PRE and/or the radiographic image P for the new imaging are displayed in the part of the screen H2, and the operator can change the display by the operation so that the preview image P_PRE and/or the radiographic image P for the new imaging are not displayed in the part of the screen H2.

The operator such as the radiologist can substantially judge success and failure of the imaging (i.e. necessity of retake; the same shall apply hereinafter) when glancing at the preview image P_PRE displayed in the display working space S having a large region. Concretely, the operator can judge/predict whether the radiographic image P can be confirmed, without adjustment, by the predetermined image processing, or can be confirmed by partially changing (i.e. executing the image quality adjustment) a parameter(s) of the predetermined image processing.

Therefore, if the preview images P, which are successively produced according to the progress of the imaging, are always displayed in the display working space S, the operator such as the radiologist can judge the success and failure of the imaging with accuracy by looking at the large image. Such configuration is effective, for example, in a situation that in an operation mode where one (1) operator confirms the images captured by a plurality of operators, the operator who confirms the images wishes to prioritize early judgment/prediction about the successively-produced preview images P_PRE and to postpone the confirming processing of the radiographic images P corresponding to these preview images P_PRE.

At that time, there may be adopted a configuration where the thumbnail image PT produced from the preview image P_PRE is displayed in the space ST at the same time as the display of one (1) preview image P_PRE in the display working space S, and when a time (e.g. a few seconds) necessary for the judgment and/or prediction by the operator such as the radiologist has passed since the preview image P_PRE is displayed in the display working space S, the focus display of the thumbnail image PT moves to the next position.

Alternatively, there may be adopted a configuration where when a time (e.g. a few seconds) necessary for the judgment and/or prediction by the operator has passed since one (1) preview image P_PRE is displayed in the display working space S, the thumbnail image PT produced from the preview image P_PRE is displayed in the space ST and the focus display of the thumbnail image PT moves to the next position.

In the above case, because each of the radiographic images P has not been subjected to the confirming process (including the above-described "deemed confirmation" processing; the same shall apply hereinafter), when the operator moves the focus display to one (1) thumbnail image PT by clicking the thumbnail image PT after completing the confirmation of all the preview images P_PRE by sight, if the radiographic image P corresponding to the preview image P_PRE of the thumbnail image PT displayed in the focused manner has been already generated, the radiographic image P is displayed in the display working space S.

Alternatively, after the confirmation of all the preview images P_PRE by sight has been completed, the console 58 automatically starts the processing of each of the radiographic images P, and subsequently the radiographic image P is subjected to the confirming process. It is needless to say that which of the processes is performed depends on ability of processing of the CPU of the console 58 or the like.

Incidentally, in the case of this system, because there may be a case that the operator forgets to execute the confirming process and transmits the radiographic image P to an external device such as the PACS, as described above, it is preferable that the console 58 informs the operator of the fact that the radiographic image P is going to be transmitted in the unconfirmed state by a sound, message, or the like.

Moreover, also in the first transition mode, in place of the image confirming process, it is possible to perform the processing up to the above-described judgment/prediction about the preview image P_PRE and stop the processing, and when the preview image P_PRE is approved, to move the focus display to the icon I corresponding to the next imaging and/or the space ST. Also in this case, similarly to the above, the image confirming processes of all the radiographic images P are performed at once at the end.

Incidentally, it is indisputable that the present invention is not limited to the above embodiments and variations, and can be arbitrary changed without departing from the spirit of the present invention.

The present U.S. patent application claims a priority under the Paris Convention of Japanese patent application No. 2013-221700 filed on Oct. 25, 2014, in which all contents of this application are disclosed, and which shall be a basis of correction of an incorrect translation.

What is claimed is:

1. A console which resisters or obtains imaging order information regarding a radiographic image imaging, and generates a radiographic image based on image data when the image data is transmitted to the console, the console comprising:
    a display section capable of displaying at least an icon corresponding to the imaging order information and a thumbnail image of the generated radiographic image,
    wherein the console performs a focus display of the icon corresponding to the imaging order information regarding a currently-performed imaging, the focus display having a different mode from a display mode of another icon, and when the currently-performed imaging ends, moves the focus display of the icon to the icon corresponding to the imaging order information regarding a next imaging,
    wherein the console performs a focus display of the thumbnail image of the generated radiographic image, the focus display including a graphical focus on the thumbnail image, having a different mode from a display mode of another thumbnail image, and after a confirming process to the radiographic image or when a predetermined time has passed since the focus display has been performed, moves the focus display of the thumbnail image to a position, on the display section, at which the thumbnail image of the radiographic image generated based on the image data obtained by the next imaging is to be displayed,
    wherein the console includes, as a transition mode of the focus display, a first transition mode in which a transition of the focus display of the icon and a transition of the focus display of the thumbnail image are performed concurrently, and a second transition mode in which each of the transition of the focus display of the icon and the transition of the focus display of the thumbnail image is independently from each other, and
    wherein the transition mode of the focus display is capable of being switched between the first transition mode and the second transition mode.

2. The console of claim 1, wherein the transition mode of the focus display is set to the first transition mode or the second transition mode depending on an operator who executes processing by using the console.

3. The console of claim 1, wherein the transition mode of the focus display is set to the first transition mode or the second transition mode depending on whether an operator who executes the imaging in an imaging room is same as or different from an operator who executes the confirming process of the radiographic image on the console.

4. The console of claim 3, wherein when the operator who execute the imaging in an imaging room is different from the operator who executes the confirming process of the radiographic image on the console, the transition mode of the focus display is set to the second transition mode, and the console is configured to prohibit the operator from moving the focus display of the icon, but to allow the operator to execute the confirming process of the radiographic image,
    wherein a portable terminal carried by the operator who executes the imaging in the imaging room is configured to display the preview image based on the image data transmitted from a radiographic image capturing apparatus, on a screen of the portable terminal, and
    wherein the portable terminal is configured to display the icon same as the icon displayed in the console, on the screen of the portable terminal, and to allow the operator to move the focus display of the icon.

5. The console of claim 1, wherein the transition mode of the focus display is set to the first transition mode or the second transition mode depending on a use mode of the console.

6. A radiographic image capturing system comprising:
    the console of claim 1;
    a radiation generator which emits radiation to an object; and
    a radiographic image capturing apparatus which includes a plurality of radiation detecting elements arranged in a two-dimensional state, and reads out, as the image data, electric charge occurring in the radiation detection elements upon radiation emission.

7. A radiographic image capturing system comprising:
    the console of claim 2; and
    a management apparatus connected to the console,
    wherein in place of the console, the management apparatus sets the transition mode of the focus display to the first transition mode or the second transition mode, depending on the operator who executes processing by using the console, or depending on whether the operator who executes the imaging in an imaging room is same as or different from the operator who executes the confirming process of the radiographic image on the console, or depending on a use mode of the console.

* * * * *